US008840676B2

(12) United States Patent
Belew et al.

(10) Patent No.: US 8,840,676 B2
(45) Date of Patent: Sep. 23, 2014

(54) MODULAR TRIAL HEADS FOR A PROSTHETIC

(75) Inventors: Kevin W. Belew, Hernando, MS (US); James C. Gatewood, Memphis, TN (US); Luke A. Gibson, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 28 days.

(21) Appl. No.: 13/319,197

(22) PCT Filed: May 7, 2010
(Under 37 CFR 1.47)

(86) PCT No.: PCT/US2010/034058
§ 371 (c)(1),
(2), (4) Date: Apr. 23, 2012

(87) PCT Pub. No.: WO2010/129880
PCT Pub. Date: Nov. 11, 2010

(65) Prior Publication Data
US 2012/0239160 A1   Sep. 20, 2012

Related U.S. Application Data

(60) Provisional application No. 61/176,458, filed on May 7, 2009.

(51) Int. Cl.
*A61F 2/32* (2006.01)
*A61F 2/46* (2006.01)
*A61F 2/30* (2006.01)
*A61F 2/36* (2006.01)

(52) U.S. Cl.
CPC ..... *A61F 2/4684* (2013.01); *A61F 2002/30828* (2013.01); *A61F 2002/3617* (2013.01); *A61F 2002/30354* (2013.01); *A61F 2002/30598* (2013.01); *A61F 2002/30616* (2013.01); *A61F 2250/0063* (2013.01); *A61F 2002/365* (2013.01); *A61F 2002/3053* (2013.01); *A61F 2/36* (2013.01); *A61F 2002/30487* (2013.01); *A61F 2002/30611* (2013.01); *A61F 2220/0025* (2013.01); *A61F 2250/0064* (2013.01); *A61F 2002/305* (2013.01); *A61F 2002/30774* (2013.01); *A61F 2002/30495* (2013.01); *A61F 2220/0033* (2013.01); *A61F 2002/3652* (2013.01); *A61F 2002/30822* (2013.01); *A61F 2002/3611* (2013.01)
USPC ........................................ 623/22.15

(58) Field of Classification Search
USPC .......... 623/22.17, 22.18, 22.21, 22.41, 22.42, 623/23.11, 23.15, 21.15, 21.16, 623/22.11–22.15, 22.4–22.46
See application file for complete search history.

(56) References Cited

U.S. PATENT DOCUMENTS 3,466,670 A * 9/1969 Christiansen ............... 623/22.43
3,584,318 A * 6/1971 Scales et al. ............... 623/23.43
(Continued)

FOREIGN PATENT DOCUMENTS

EP   1 415 620 A2   5/2004
WO   WO 2008/144725 A1   11/2008

*Primary Examiner* — Alvin Stewart
(74) *Attorney, Agent, or Firm* — Krieg DeVault LLP

(57) ABSTRACT

A prosthesis trial system includes at least one head member having an outer surface and a cavity configured to mate with an exterior surface of a stem member. The prosthesis trial system further includes at least one shell member having an inner surface configured to mate with the outer surface of the at least one head member.

29 Claims, 23 Drawing Sheets

(56) References Cited

U.S. PATENT DOCUMENTS

| | | | | |
|---|---|---|---|---|
| 3,658,056 A * | 4/1972 | Huggler et al. | | 623/22.43 |
| 3,813,699 A * | 6/1974 | Giliberty | | 623/22.17 |
| 3,818,512 A * | 6/1974 | Shersher | | 623/22.15 |
| 3,863,273 A * | 2/1975 | Averill | | 623/22.17 |
| 3,889,299 A * | 6/1975 | Osborne et al. | | 623/22.17 |
| 3,925,824 A * | 12/1975 | Freeman et al. | | 623/23.12 |
| 3,987,499 A * | 10/1976 | Scharbach et al. | | 623/17.11 |
| 4,004,300 A * | 1/1977 | English | | 623/22.17 |
| 4,032,994 A * | 7/1977 | Frey | | 623/22.45 |
| 4,135,517 A * | 1/1979 | Reale | | 606/86 R |
| 4,170,794 A * | 10/1979 | Zeibig et al. | | 623/22.45 |
| 4,172,296 A * | 10/1979 | D'Errico | | 623/22.28 |
| 4,225,981 A * | 10/1980 | Zeibig | | 623/22.43 |
| 4,279,041 A * | 7/1981 | Buchholz | | 623/19.12 |
| 4,318,190 A * | 3/1982 | Cortesi | | 623/22.43 |
| 4,328,593 A * | 5/1982 | Sutter et al. | | 623/23.42 |
| 4,332,036 A * | 6/1982 | Sutter et al. | | 623/23.42 |
| 4,551,863 A * | 11/1985 | Murray | | 623/22.43 |
| 4,624,674 A * | 11/1986 | Pappas et al. | | 623/22.19 |
| 4,676,799 A * | 6/1987 | Legrand | | 623/22.19 |
| 4,687,488 A * | 8/1987 | Frey | | 623/22.45 |
| 4,718,911 A * | 1/1988 | Kenna | | 623/22.29 |
| 4,770,658 A * | 9/1988 | Geremakis | | 623/22.19 |
| 4,770,659 A * | 9/1988 | Kendall | | 623/22.19 |
| 4,784,663 A * | 11/1988 | Kenna | | 623/22.29 |
| 4,795,469 A * | 1/1989 | Oh | | 623/22.27 |
| 4,795,471 A * | 1/1989 | Oh | | 623/22.19 |
| 4,822,369 A * | 4/1989 | Oueveau et al. | | 623/22.14 |
| 4,842,605 A * | 6/1989 | Sonnerat et al. | | 623/22.45 |
| 4,911,720 A * | 3/1990 | Collier | | 623/23.12 |
| 4,911,723 A * | 3/1990 | Menschik | | 623/22.15 |
| 4,921,500 A * | 5/1990 | Averill et al. | | 623/22.45 |
| 4,936,855 A * | 6/1990 | Sherman | | 623/22.2 |
| 4,936,861 A * | 6/1990 | Muller et al. | | 623/22.24 |
| 4,950,299 A * | 8/1990 | Noiles | | 623/22.18 |
| 4,960,427 A * | 10/1990 | Noiles | | 623/22.18 |
| 4,963,154 A * | 10/1990 | Anapliotis et al. | | 623/22.28 |
| 4,963,155 A * | 10/1990 | Lazzeri et al. | | 623/22.42 |
| 4,964,869 A * | 10/1990 | Auclair et al. | | 623/22.43 |
| 4,969,910 A * | 11/1990 | Frey et al. | | 623/22.33 |
| 4,978,356 A * | 12/1990 | Noiles | | 623/23.4 |
| 5,019,105 A * | 5/1991 | Wiley | | 623/22.29 |
| 5,074,881 A * | 12/1991 | Thull et al. | | 623/22.3 |
| 5,092,897 A * | 3/1992 | Forte | | 623/22.18 |
| 5,108,446 A * | 4/1992 | Wagner et al. | | 623/22.28 |
| 5,156,624 A * | 10/1992 | Barnes | | 623/22.45 |
| 5,156,626 A * | 10/1992 | Broderick et al. | | 623/22.12 |
| 5,226,917 A * | 7/1993 | Schryver | | 623/22.37 |
| 5,258,033 A * | 11/1993 | Lawes et al. | | 623/23.13 |
| 5,362,311 A * | 11/1994 | Amino et al. | | 623/22.45 |
| 5,413,610 A * | 5/1995 | Amino et al. | | 623/22.43 |
| 5,425,779 A * | 6/1995 | Schlosser et al. | | 623/22.2 |
| 5,458,649 A * | 10/1995 | Spotorno et al. | | 623/22.27 |
| 5,458,650 A * | 10/1995 | Carret et al. | | 623/22.25 |
| 5,507,828 A * | 4/1996 | Maumy et al. | | 623/22.26 |
| 5,549,691 A * | 8/1996 | Harwin | | 623/22.37 |
| 5,549,693 A * | 8/1996 | Roux et al. | | 623/22.14 |
| 5,549,695 A * | 8/1996 | Spotorno et al. | | 623/22.35 |
| 5,549,696 A * | 8/1996 | Willi | | 623/22.28 |
| 5,549,700 A * | 8/1996 | Graham et al. | | 623/22.14 |
| 5,549,704 A * | 8/1996 | Sutter | | 623/23.13 |
| 5,641,323 A * | 6/1997 | Caldarise | | 623/22.18 |
| 5,658,348 A * | 8/1997 | Rohr, Jr. | | 623/22.29 |
| 5,702,456 A * | 12/1997 | Pienkowski | | 128/898 |
| 5,725,591 A * | 3/1998 | DeCarlo et al. | | 623/22.29 |
| 5,735,901 A * | 4/1998 | Maumy et al. | | 128/898 |
| 5,800,554 A * | 9/1998 | Scholz | | 623/22.43 |
| 5,865,850 A * | 2/1999 | Matthews | | 623/22.43 |
| 5,879,401 A * | 3/1999 | Besemer et al. | | 623/22.28 |
| 5,879,406 A * | 3/1999 | Lilley | | 623/22.15 |
| 5,904,720 A * | 5/1999 | Farrar et al. | | 623/22.15 |
| 5,935,175 A * | 8/1999 | Ostiguy et al. | | 623/22.28 |
| 6,093,208 A * | 7/2000 | Tian | | 623/22.2 |
| 6,126,695 A * | 10/2000 | Semlitsch | | 623/22.15 |
| 6,129,765 A * | 10/2000 | Lopez et al. | | 623/22.15 |
| 6,136,036 A * | 10/2000 | Scholz | | 623/23.11 |
| 6,152,961 A * | 11/2000 | Ostiguy et al. | | 623/22.28 |
| 6,162,256 A * | 12/2000 | Ostiguy et al. | | 623/22.26 |
| 6,187,049 B1 * | 2/2001 | Fujikawa et al. | | 623/22.4 |
| 6,206,929 B1 * | 3/2001 | Ochoa et al. | | 623/22.17 |
| 6,336,941 B1 * | 1/2002 | Subba Rao et al. | | 623/22.42 |
| 6,355,068 B1 * | 3/2002 | Doubler et al. | | 623/22.42 |
| 6,379,389 B1 * | 4/2002 | Koch | | 623/22.28 |
| 6,423,097 B2 * | 7/2002 | Rauscher | | 623/21.16 |
| 6,443,992 B2 * | 9/2002 | Lubinus | | 623/23.18 |
| 6,454,808 B1 * | 9/2002 | Masada | | 623/21.15 |
| 6,475,243 B1 * | 11/2002 | Sheldon et al. | | 623/22.28 |
| 6,660,040 B2 * | 12/2003 | Chan et al. | | 623/22.21 |
| 6,679,917 B2 * | 1/2004 | Ek | | 623/20.14 |
| 6,682,565 B1 * | 1/2004 | Krishnan | | 623/21.16 |
| 6,682,566 B2 * | 1/2004 | Draenert | | 623/22.24 |
| 6,706,073 B2 * | 3/2004 | Draenert et al. | | 623/22.46 |
| 6,761,741 B2 * | 7/2004 | Iesaka | | 623/22.26 |
| 6,802,275 B2 * | 10/2004 | Schmidt | | 114/361 |
| 6,811,569 B1 * | 11/2004 | Afriat et al. | | 623/22.32 |
| 6,860,903 B2 * | 3/2005 | Mears et al. | | 623/22.11 |
| 6,875,238 B1 * | 4/2005 | Price | | 623/23.11 |
| 6,953,478 B2 * | 10/2005 | Bouttens et al. | | 623/19.11 |
| 6,969,406 B2 * | 11/2005 | Tornier | | 623/19.13 |
| 6,976,999 B2 * | 12/2005 | Charlebois et al. | | 623/16.11 |
| 7,108,720 B2 * | 9/2006 | Hanes | | 623/22.21 |
| 7,160,332 B2 * | 1/2007 | Frederick et al. | | 623/22.29 |
| 7,179,297 B2 * | 2/2007 | McLean | | 623/22.11 |
| 7,192,449 B1 * | 3/2007 | McQueen et al. | | 623/22.25 |
| 7,368,065 B2 * | 5/2008 | Yang et al. | | 216/83 |
| 7,458,989 B2 * | 12/2008 | Banks et al. | | 623/22.45 |
| 7,534,271 B2 | 5/2009 | Ries et al. | | |
| 7,708,783 B2 * | 5/2010 | Richards | | 623/22.15 |
| 7,780,737 B2 * | 8/2010 | Bonnard et al. | | 623/21.11 |
| 7,780,739 B2 * | 8/2010 | Lakin et al. | | 623/22.17 |
| 7,794,504 B2 * | 9/2010 | Case | | 623/22.21 |
| 7,918,895 B2 * | 4/2011 | Isch et al. | | 623/22.12 |
| 8,007,539 B2 * | 8/2011 | Slone | | 623/22.15 |
| 8,034,116 B2 * | 10/2011 | Vander Meulen et al. | | 623/22.43 |
| 8,052,758 B1 * | 11/2011 | Winslow | | 623/22.42 |
| 8,070,823 B2 * | 12/2011 | Kellar et al. | | 623/23.4 |
| 8,142,512 B2 * | 3/2012 | Brooks et al. | | 623/23.4 |
| 8,157,870 B2 * | 4/2012 | Kropf et al. | | 623/23.12 |
| 8,177,851 B2 * | 5/2012 | Drescher | | 623/22.29 |
| 8,211,182 B2 * | 7/2012 | Linares | | 623/22.15 |
| 8,277,457 B1 * | 10/2012 | Burgi et al. | | 606/91 |
| 8,308,810 B2 * | 11/2012 | Meridew | | 623/22.19 |
| 8,308,812 B2 * | 11/2012 | Kellar et al. | | 623/23.4 |
| 8,377,376 B2 * | 2/2013 | Baege et al. | | 422/34 |
| 8,556,984 B2 * | 10/2013 | Calamel | | 623/22.13 |
| 8,585,769 B2 * | 11/2013 | Vankoski et al. | | 623/22.24 |
| 2002/0052659 A1 * | 5/2002 | Hayes et al. | | 623/22.24 |
| 2002/0052661 A1 * | 5/2002 | Spotorno et al. | | 623/23.48 |
| 2002/0068980 A1 * | 6/2002 | Serbousek et al. | | 623/22.29 |
| 2002/0143402 A1 * | 10/2002 | Steinberg | | 623/22.16 |
| 2002/0193882 A1 * | 12/2002 | Koller | | 623/23.12 |
| 2003/0074077 A1 * | 4/2003 | Taylor | | 623/22.26 |
| 2003/0074083 A1 * | 4/2003 | LeGros et al. | | 623/23.35 |
| 2003/0105529 A1 * | 6/2003 | Synder et al. | | 623/22.24 |
| 2003/0114935 A1 * | 6/2003 | Chan et al. | | 623/22.21 |
| 2003/0171817 A1 * | 9/2003 | Rambert et al. | | 623/22.17 |
| 2004/0034433 A1 * | 2/2004 | Chan et al. | | 623/23.39 |
| 2004/0054418 A1 * | 3/2004 | McLean et al. | | 623/22.17 |
| 2004/0054421 A1 * | 3/2004 | McLean | | 623/23.11 |
| 2004/0059429 A1 * | 3/2004 | Amin et al. | | 623/23.51 |
| 2004/0078083 A1 * | 4/2004 | Gibbs et al. | | 623/22.17 |
| 2004/0093090 A1 * | 5/2004 | Barbieri et al. | | 623/22.3 |
| 2004/0122524 A1 * | 6/2004 | Hunter et al. | | 623/22.18 |
| 2004/0193278 A1 | 9/2004 | Maroney et al. | | |
| 2004/0199257 A1 * | 10/2004 | Dooney | | 623/22.24 |
| 2004/0204767 A1 * | 10/2004 | Park et al. | | 623/22.17 |
| 2004/0225370 A1 * | 11/2004 | Cruchet et al. | | 623/22.18 |
| 2005/0004678 A1 * | 1/2005 | Richards | | 623/22.28 |
| 2005/0010303 A1 * | 1/2005 | Nogier | | 623/22.26 |
| 2005/0149199 A1 * | 7/2005 | Steinberg | | 623/22.23 |
| 2005/0177244 A1 * | 8/2005 | Steinberg | | 623/22.17 |
| 2006/0009857 A1 * | 1/2006 | Gibbs et al. | | 623/23.4 |
| 2006/0167557 A1 * | 7/2006 | Terrill | | 623/22.43 |
| 2006/0188845 A1 * | 8/2006 | Serafin et al. | | 433/173 |

(56) References Cited

U.S. PATENT DOCUMENTS

| | | | | |
|---|---|---|---|---|
| 2006/0200247 | A1* | 9/2006 | Charrois | 623/19.11 |
| 2006/0217815 | A1* | 9/2006 | Gibbs et al. | 623/22.17 |
| 2006/0259148 | A1* | 11/2006 | Bar-Ziv | 623/19.14 |
| 2007/0005145 | A1* | 1/2007 | Banks et al. | 623/23.42 |
| 2007/0106390 | A1* | 5/2007 | Richards | 623/22.18 |
| 2007/0106392 | A1* | 5/2007 | Servidio et al. | 623/22.28 |
| 2007/0198096 | A1* | 8/2007 | Wort | 623/23.42 |
| 2007/0219640 | A1* | 9/2007 | Steinberg | 623/22.12 |
| 2007/0270975 | A1* | 11/2007 | Taylor et al. | 623/23.5 |
| 2008/0228282 | A1* | 9/2008 | Brodowski | 623/22.11 |
| 2008/0262625 | A1* | 10/2008 | Spriano et al. | 623/22.15 |
| 2009/0043397 | A1* | 2/2009 | Park | 623/23.11 |
| 2009/0088865 | A1* | 4/2009 | Brehm | 623/22.21 |
| 2009/0093887 | A1* | 4/2009 | Walter et al. | 623/22.11 |
| 2009/0276052 | A1* | 11/2009 | Regala et al. | 623/18.11 |
| 2009/0287312 | A1* | 11/2009 | Berger et al. | 623/22.29 |
| 2010/0049327 | A1* | 2/2010 | Isch et al. | 623/19.12 |
| 2010/0063589 | A1* | 3/2010 | Tepic | 623/17.11 |
| 2010/0070046 | A1* | 3/2010 | Steinberg | 623/22.25 |
| 2010/0100193 | A1* | 4/2010 | White | 623/22.43 |
| 2010/0121458 | A1* | 5/2010 | Ledger et al. | 623/23.12 |
| 2010/0131073 | A1* | 5/2010 | Meridew et al. | 623/22.28 |
| 2010/0145466 | A1* | 6/2010 | Slone | 623/22.15 |
| 2010/0161069 | A1* | 6/2010 | Ragbir | 623/22.11 |
| 2010/0161072 | A1* | 6/2010 | Drescher | 623/22.29 |
| 2010/0174380 | A1* | 7/2010 | Lewis | 623/22.11 |
| 2010/0179663 | A1* | 7/2010 | Steinberg | 623/22.24 |
| 2010/0185297 | A1* | 7/2010 | Steinberg | 623/22.21 |
| 2010/0234965 | A1* | 9/2010 | Dalla Pria et al. | 623/22.28 |
| 2010/0256758 | A1* | 10/2010 | Gordon et al. | 623/16.11 |
| 2010/0262255 | A1* | 10/2010 | Gladdish et al. | 623/22.21 |
| 2010/0268227 | A1* | 10/2010 | Tong et al. | 606/60 |
| 2011/0009964 | A1* | 1/2011 | Schwartz et al. | 623/14.12 |
| 2011/0015753 | A1* | 1/2011 | Meridew | 623/22.24 |
| 2011/0106271 | A1* | 5/2011 | Regala et al. | 623/23.4 |
| 2011/0118848 | A1* | 5/2011 | Faccioli et al. | 623/22.11 |
| 2011/0243650 | A1* | 10/2011 | Linares | 403/122 |
| 2011/0257757 | A1* | 10/2011 | Popoola et al. | 623/22.15 |
| 2012/0109334 | A1* | 5/2012 | Forsell | 623/23.14 |
| 2012/0143343 | A1* | 6/2012 | Meridew et al. | 623/22.15 |
| 2012/0150314 | A1* | 6/2012 | Forsell | 623/23.12 |
| 2012/0165952 | A1* | 6/2012 | Stinnette | 623/22.15 |
| 2012/0179269 | A1* | 7/2012 | Hume et al. | 623/22.15 |
| 2012/0180300 | A1* | 7/2012 | Gradel | 29/447 |
| 2012/0185059 | A1* | 7/2012 | Vankoski et al. | 623/22.24 |
| 2012/0209397 | A1* | 8/2012 | Richardson | 623/22.15 |
| 2012/0209398 | A1* | 8/2012 | Richardson et al. | 623/22.17 |
| 2012/0265320 | A1* | 10/2012 | Kranz et al. | 623/23.26 |
| 2013/0060346 | A1* | 3/2013 | Collins | 623/23.12 |
| 2013/0073051 | A1* | 3/2013 | Meridew | 623/22.26 |
| 2013/0079887 | A1* | 3/2013 | Grostefon et al. | 623/22.24 |
| 2013/0184832 | A1* | 7/2013 | Haidukewych | 623/22.32 |
| 2013/0190770 | A1* | 7/2013 | Penenberg et al. | 606/91 |
| 2013/0245781 | A1* | 9/2013 | Allen et al. | 623/22.28 |

\* cited by examiner

MODULAR TRIAL HEADS FOR A PROSTHETIC

CROSS REFERENCE TO RELATED APPLICATIONS

This application is a U.S. National Phase of International PCT Application No. PCT/US2010/034058 filed on May 7, 2010, which claims the benefit of priority of U.S. Provisional Application No. 61/176,458 filed on May 7, 2009, the contents of each application hereby incorporated by reference in its entirety.

FIELD OF INVENTION

The present application relates to the field of orthopedics. More particularly, the present application relates to a trial prosthesis for a femur.

BACKGROUND

A successful hip replacement or arthroplasty procedure results, in part, from selection of prosthetic joint components that are dimensioned and positioned to correspond with the anatomy of a particular patient. The component selection process may include a pre-operative analysis of joint images. The component selection process also may include temporary fixation of one or more provisional components to a bone prior to permanent fixation of the prosthetic. These provisional components may be referred to as "trials," "trial heads," or "trial prostheses." After a satisfactory trial prosthesis is found, it is removed and replaced with a permanent prosthesis of the same dimensions.

SUMMARY OF THE INVENTION

In one embodiment, a femoral trial system may be used with a plurality of stems. The femoral trial system includes a plurality of head members, each head member having an outer surface, and a cavity configured to mate with an exterior surface of a stem component, where the cavity has at least one sidewall. Each head member further includes a first set of barbs disposed on the sidewall of the cavity at a first depth, and a second set of barbs disposed on the sidewall of the cavity at a second depth spaced apart from the first depth. The femoral trial system also includes a plurality of shell members, each shell member having an inner surface configured to mate with an outer surface of at least one of the plurality of head members.

In another embodiment, a prosthetic instrument may be used in a trial fitting of a medical implant. The instrument includes a head member having a cavity disposed therein, wherein the cavity is configured to mate with an exterior surface of a stem component, and wherein the cavity has at least one sidewall. The instrument also includes a first barb disposed on the sidewall of the cavity at a first depth, and a second barb disposed on the sidewall of the cavity at a second depth different than the first depth.

In another embodiment, a prosthesis trial system includes at least one head member having an outer surface and a cavity configured to mate with an exterior surface of a stem member. The prosthesis trial system further includes at least one shell member having an inner surface configured to mate with the outer surface of the at least one head member.

BRIEF DESCRIPTION OF THE DRAWINGS

In the accompanying drawings, structures are illustrated that, together with the detailed description provided below, describe exemplary embodiments of the claimed invention.

In the drawings and description that follows, like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

Figure 1:
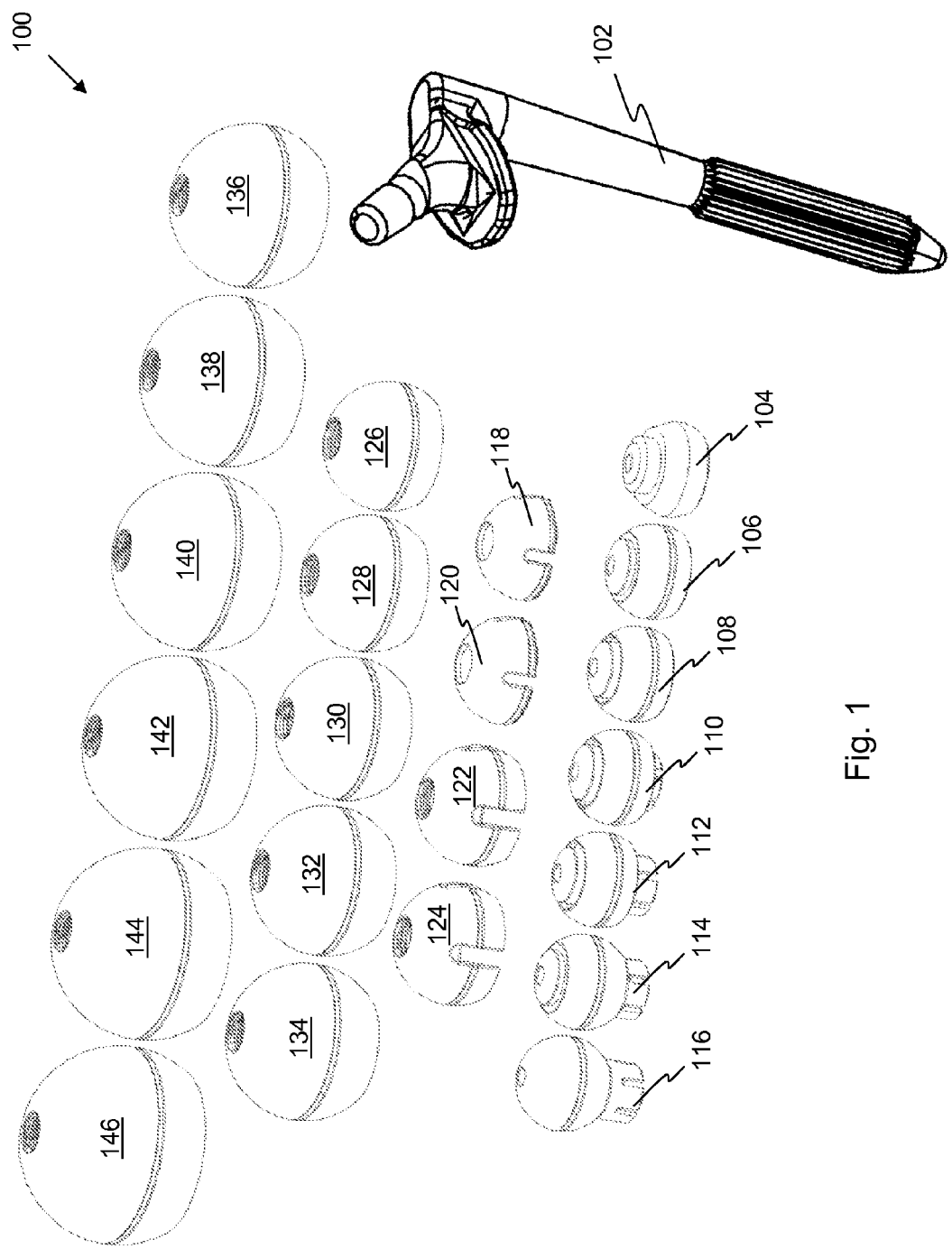
FIG. 1 is a perspective view of components of a femoral trial system.

FIG. 1 illustrates one embodiment of a femoral trial system 100 including a stem 102, a plurality of head members 104-116, and a plurality of shell members 118-146. In the illustrated embodiment, the femoral trial system includes a single stem 102, seven head members 104-116, and fifteen shell members 118-146. In alternative embodiments (not shown), any number of stems, head members, and shell members may be employed. Although the system is described herein as a femoral trial system, it should be understood that similar instrumentation may be used for other prosthetic trial systems, such as a shoulder trial system.

The stem 102 includes an elongated shaft configured to be inserted in a cavity formed in a femur of a subject. The stem further includes a neck portion configured to mate with a head member. The stem 102 may be a commercially available stem. The stem 102 may be constructed of any material suitable for prosthetic use, including, without limitation: cobalt chrome, titanium, and stainless steel alloys.

Each of the head members 104-116 is configured to engage, or mate with, the stem 102. In the illustrated embodiment, each of the head members 104-116 has a circular cross-section. Each head member 104-116 has an outer surface that may have a spherical portion or a hemispherical portion. In one embodiment, the outer surface of each of the head members 104-116 has substantially the same maximum diameter. In one specific embodiment, the outer surface of each of the head members 104-116 has a maximum diameter of 28 mm. In alternative embodiments, different dimensions may be employed.

Each of the head members 104-116 may be constructed of any suitable material useful for temporary surgical use. Such materials include, without limitation: polymeric materials, such as polyoxymethylene, polyetherimide, polyethylene, polypropylene, and polyphenyl sulfone. Additional materials include nylon and mixtures thereof, as well as metals, such as aluminum and stainless steel.

Each of the shell members 118-146 has an inner surface configured to engage, or mate with, the outer surface of at least one of the head members 104-116. In one embodiment, each shell member 118-146 is configured to mate with the outer surfaces of selected head members 104-116, and configured to not mate with the outer surfaces of the remaining head members 104-116.

In the illustrated embodiment, each of the shell members 118-146 has an outer surface with at least a partial spherical portion that is configured to engage a hip joint of a subject. In one embodiment, a first shell member 118 and a second shell member 120 have the same diameter. In one specific embodiment, the first shell member 118 and the second shell member 120 have diameters of 32 mm.

With continued reference to FIG. 1, a third shell member 122 and a fourth shell member 124 have the same diameter. In one specific embodiment, the third shell member 122 and the fourth shell member 124 have diameters of 36 mm. Each of the remaining shell members 126-146 is a different size. In one embodiment, a fifth shell member 126 has a diameter of 38 mm and the shell members 128-146 are increasingly larger by increments of 2 mm, such that the largest shell member 146 has a diameter of 58 mm. In alternative embodiments, different dimensions may be employed.

Each of the shell members 118-146 may be constructed of any suitable material useful for temporary surgical use. Such materials include, without limitation: polymeric materials, such as polyoxymethylene, polyetherimide, polyethylene, polypropylene, and polyphenyl sulfone. Additional materials include nylon and mixtures thereof, as well as metals, such as aluminum and stainless steel.

Figure 2A:
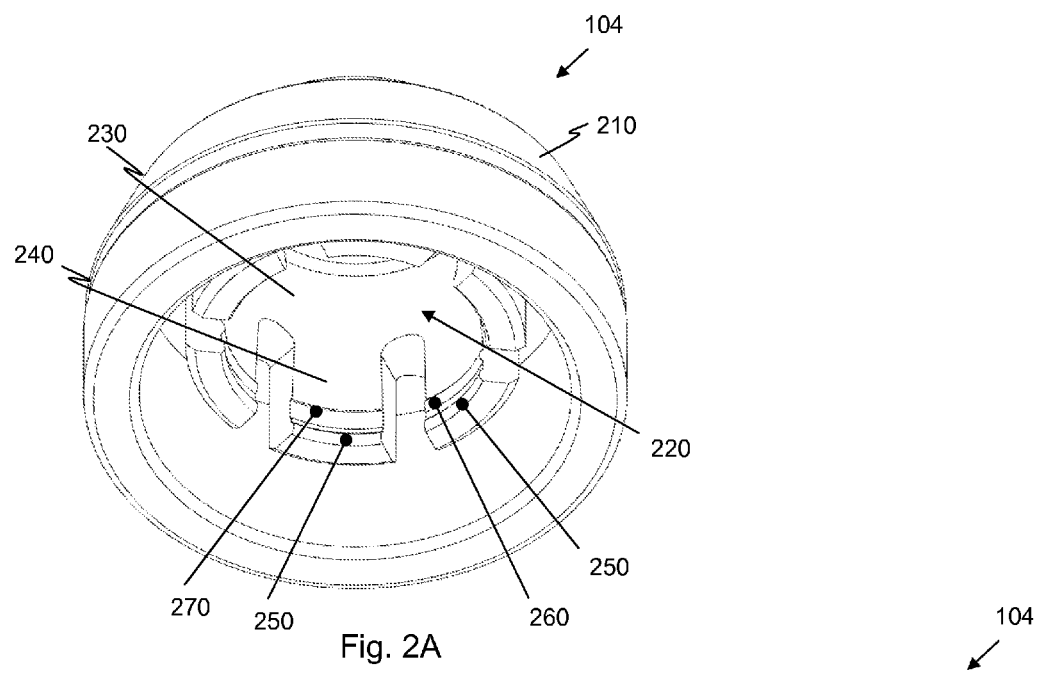
FIGS. 2A and 2B are perspective views of an exemplary head member of the femoral trial system.
Figure 2B:
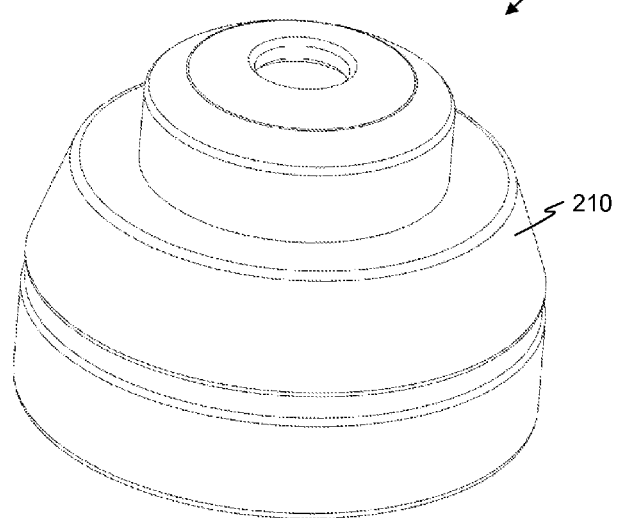

FIGS. 2A and 2B illustrate perspective views of an exemplary head member 104. The head member 104 includes an outer surface 210 and a cavity 220 defined by at least one sidewall 230. The cavity 220 is defined by walls that are configured to mate with an exterior surface of a component of the stem 102. In the illustrated embodiment, the sidewall 230 of the cavity 220 includes a plurality of spaced apart projections (or fingers) 240. The projections 240 may flex radially outward to receive the component of the stem 102 as it is inserted in the cavity 220. Although six projections 240 are shown, it should be understood that any number of projections may be employed.

The sidewall 230 includes a first set of barbs 250 disposed at a first depth and a second set of barbs 260 disposed at a second depth. The first set of barbs 250 is positioned to engage a corresponding feature on the exterior surface of a first stem, and the second set of barbs 260 is positioned to engage a corresponding feature on the exterior surface of a second stem. The first and second set of barbs 250, 260 are shown as ribs that are integral with the projections 240, and having a round profile. However, it should be understood that different projections of various geometries may be employed as barbs.

In the illustrated embodiment, certain projections 240 include both the first and second set of barbs 250, 260 and certain projections 240 include the first set of barbs 250 and a smooth surface 270 at the second depth. The projections 240 alternate between having one and two sets of barbs. In an alternative embodiment (not shown), each projection only includes a single set of barbs. In such an embodiment, the projections may alternate between having the first set of barbs and the second set of barbs. In another alternative embodiment (not shown), each projection includes both the first and second set of barbs.

Figure 3A:
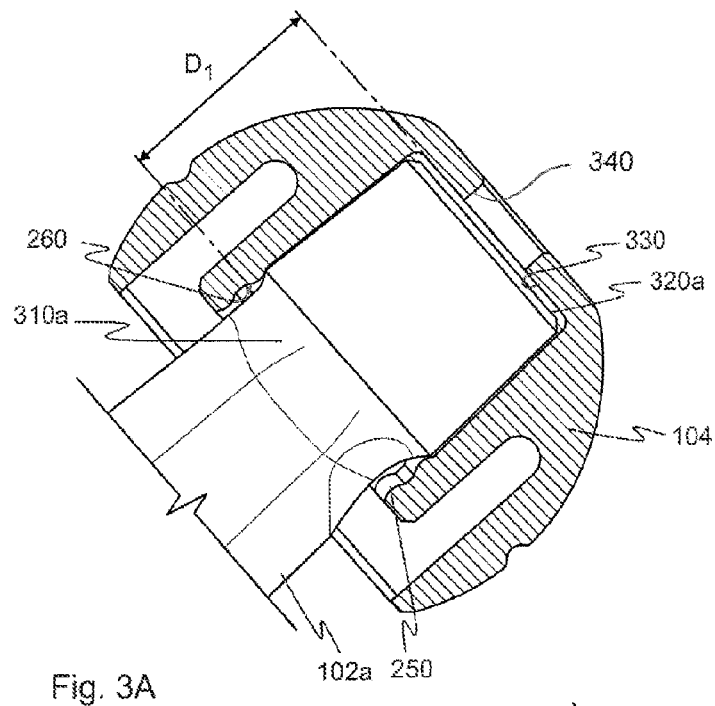
FIG. 3A is a cross-section of an exemplary head member engaging a first embodiment of a stem.

FIG. 3A is a cross-section of an exemplary head member 104 engaging a first embodiment of a stem 102a. The first embodiment of the stem 102a has a groove 310a located at a first distance $D_1$ from a top surface 320a of the first stem 102a. To mate the head member 104 with the first stem 102a, an operator slides the cavity 220 of the head member 104 over the first stem 102a. The diameter of the stem 102a is such that it causes the projections 240 of the sidewall 230 to flex radially outward. The operator then pushes the head member 104 downwards, and the first set of barbs 250 engage the groove 310a. As the operator continues to push the head member 104 downwards, the first set of barbs 250 exit the groove 310a and then the second set of barbs 260 engage the groove 310a. The first set of barbs 250 are in contact with, but not engaged with the stem 102.

When the second set of barbs 260 are engaged with the groove 310a, the head member 104 is fully mated with first stem 102a and the top surface 320a of the first stem 102a contacts a top internal surface 330 of the head member 104. The top of the head member 104 has an aperture 340 that allows the operator to view the top surface 320a of the first stem 102a, and verify that the head member 104 is fully mated with the first stem 102a. When the first set of barbs 250 engages the groove 310a of the first stem 102a, the operator can observe through the aperture 340 that the top surface 320a of the first stem 102a is spaced from the top internal surface 330, which indicates that the head member 104 is fully mated with the first stem 102a.

Figure 3B:
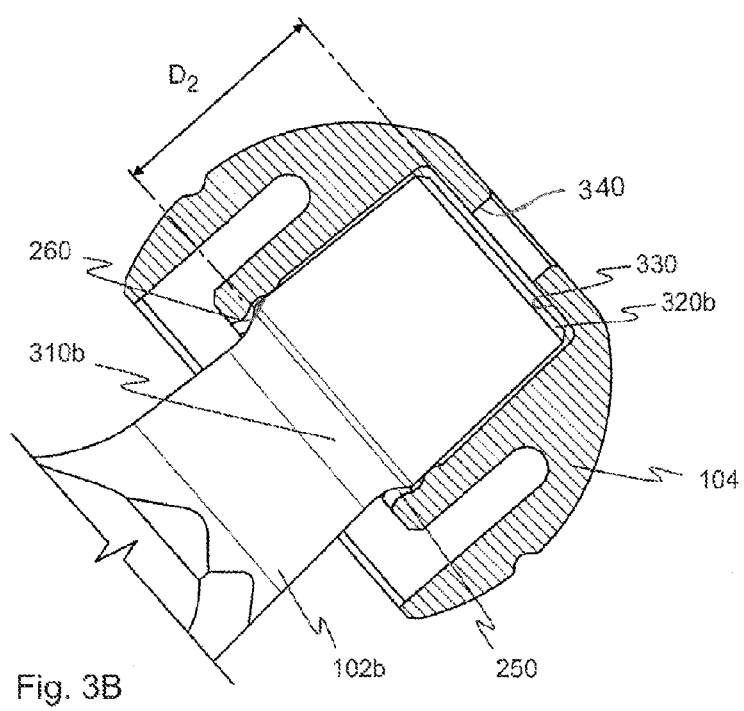
FIG. 3B is a cross-section of an exemplary head member engaging a second embodiment of a stem.

FIG. 3B is a cross-section of the head member 104 engaging a second embodiment of a stem 102b. The second embodiment of the stem 102b has a groove 310b located at a second distance $D_2$ from a top surface 320b of the second stem 102b. To mate the head member 104 with the second stem 102b, an operator slides the cavity 220 of the head member 104 over the second stem 102b. The diameter of the second stem 102b is such that it causes the projections 240 of the sidewall 230 to flex radially outward. The operator then pushes the head member 104 downwards until the first set of barbs 250 engage the groove 310b.

When the first set of barbs 250 are engaged with the groove 310b, the head member 104 is fully mated with second stem 102b and the top surface 320b of the second stem 102b contacts a top internal surface 330 of the head member 104. The operator may verify that the head member 104 is fully mated with the second stem 102b by observing through the aperture 340 of the head member 104 that the top surface 320b of the second stem 102b is in contact with the top internal surface 330 of the head member 104.

Figure 4:
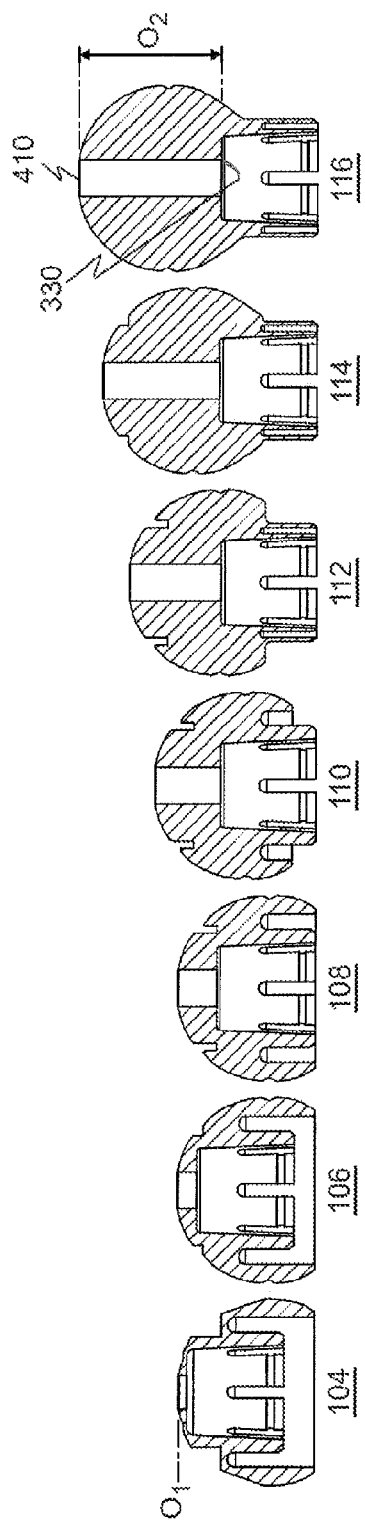
FIG. 4 is a cross-section of a plurality of head members of the femoral trial system.

FIG. 4 illustrates a cross-section of the plurality of head members 104-116 of the femoral trial system 100. Although each of the plurality of head members 104-116 has substantially the same maximum diameter, the head members differ in the distance between the top internal surface 330 and the top 410 of the outer surface 210. This distance may be referred to as the offset of the head member. For example, head member 104 has a minimal offset $O_1$ and head member 116 has a maximum offset $O_2$. Different manufacturers may have different terminology for describing these offsets. For example, under applicant's terminology, head member 104 may be described as having a −4 mm offset, head member 106 may be described as having a −3 mm offset, head member 108 may be described as having a +0 mm offset, head member 110 may be described as having a +4 mm offset, head member 112 may be described as having a +8 mm offset, head member 114 may be described as having a +11 mm offset, and head member 116 may be described as having a +15 mm offset. Another manufacturer may utilize the +0, +4 nomenclature to describe its head offsets, but its +0 may have a different dimension than the +0 head of a different manufacturer. In other terminologies, head members may be described as having an offset of A, B, C, etc.

Figure 5:
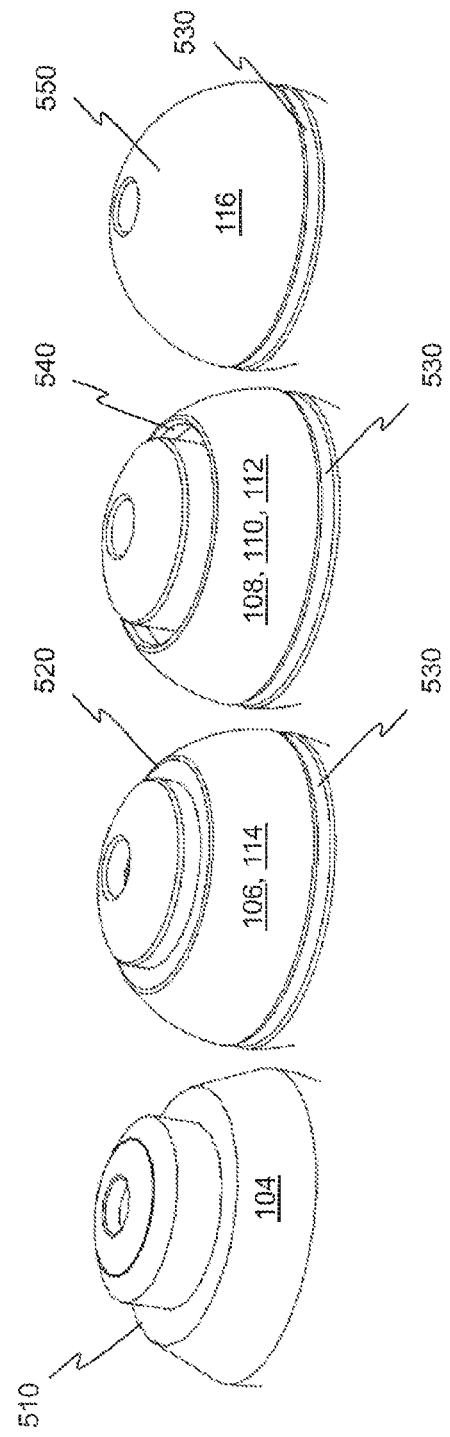
FIG. 5 is a perspective view of a plurality of head members of the femoral trial system.
Figure 6:
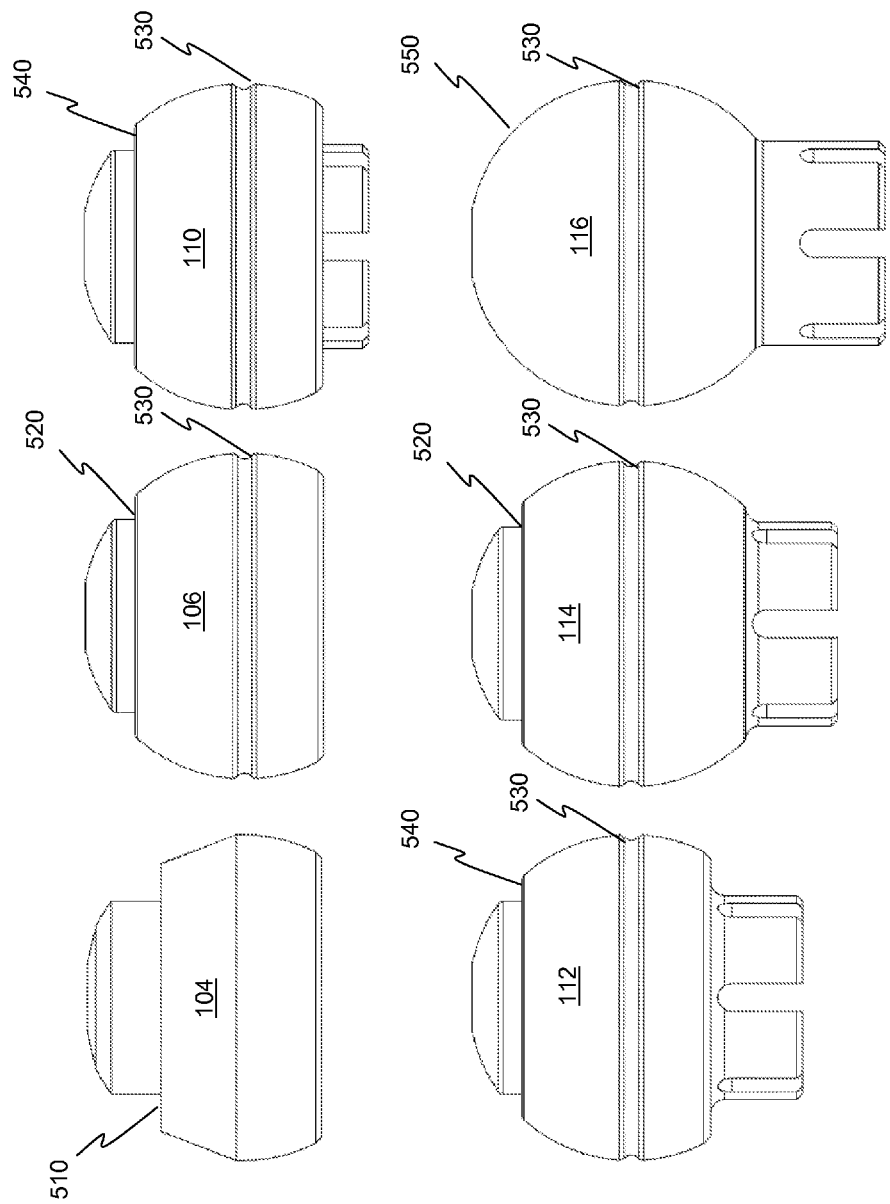
FIG. 6 is a side view of a plurality of head members of the femoral trial system.

In addition to having different offsets, head members 104-116 have different features on their outer surfaces for engaging different shell members. These features are shown in FIGS. 5 and 6, which illustrate perspective views and side views, respectively, of a plurality of exemplary head members of the femoral trial system 100. For example, head member 104 includes a flat surface 510 spaced from the top of the outer surface. Head members 106 and 114 have a flat surface 520 spaced from the top of the outer surface, but at a smaller distance than the flat surface 510 of the head member 104. Head members 106 and 114 also have the groove 530. Head members 108, 110, and 112 have a recess 540 formed in the outer surface, as well as the groove 530. Head member 116 has a substantially smooth outer surface 550 above the groove 530.

The outer surface of each head member 104-116 is configured to mate with an inner surface of selected shell members 118-146. Known commercially available permanent prostheses have a limited number of diameter and offset combinations. Accordingly, the components of the femoral trial system 100 may be configured such that a head member and shell member combination is only possible if a corresponding permanent prosthesis exists. For example, in one known permanent prostheses system, a permanent head having a 36 mm diameter and a +11 mm offset is available, but a permanent head having a 36 mm diameter and a −4 mm offset is not available. Accordingly, the components of the femoral trial system 100 may be configured such that, for example, shell member 124 has a 36 mm diameter and is configured to mate with head member 114, which has a +11 mm offset, but is configured such that it will not mate with head member 104, which has a −4 mm offset.

Figure 7:
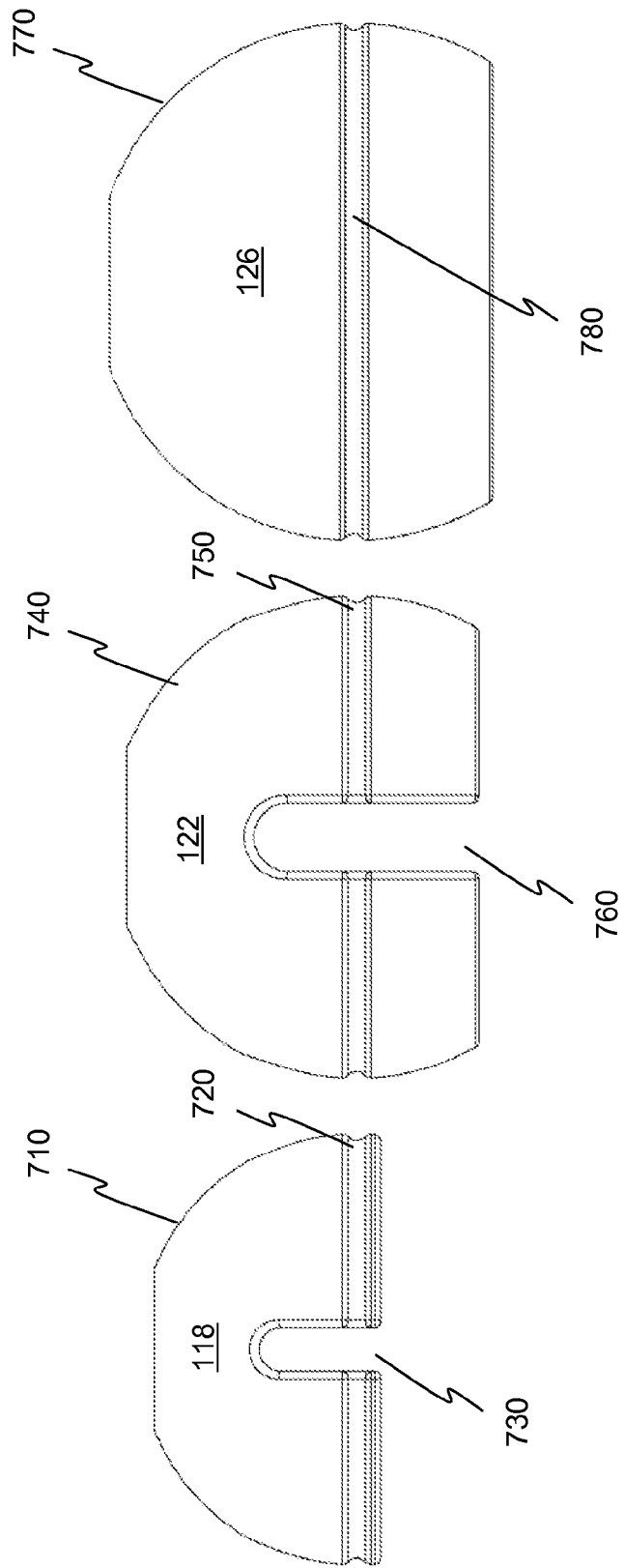
FIG. 7 is a side view of a plurality of shell members of the femoral trial system.

FIG. 7 illustrates side views of a plurality of exemplary shell members. As shown here, the shell members may have different profiles. For example, the 30 mm shell member 118 has a hemispherical outer surface 710, a groove 720, and at least one notch 730. The 34 mm shell member 122 has a partially spherical outer surface 740, a groove 750, and at least one notch 760. The 38 mm shell member 126 has a partially spherical outer surface 770 and a groove 780.

Figure 8A:
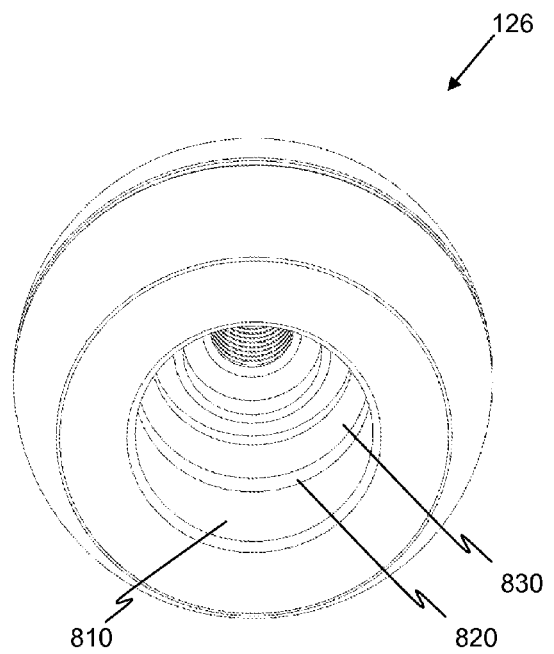
FIGS. 8A and 8B are perspective views of an exemplary shell member of the femoral trial system.

FIG. 8A illustrates a bottom perspective view of an exemplary shell member 126. The shell member 126 has an inner surface 810 configured to mate with an outer surface of a head member. The inner surface 810 includes ribs 820 and grooves 830 that correspond to features of the outer surfaces of selected head members.

Figure 8B:
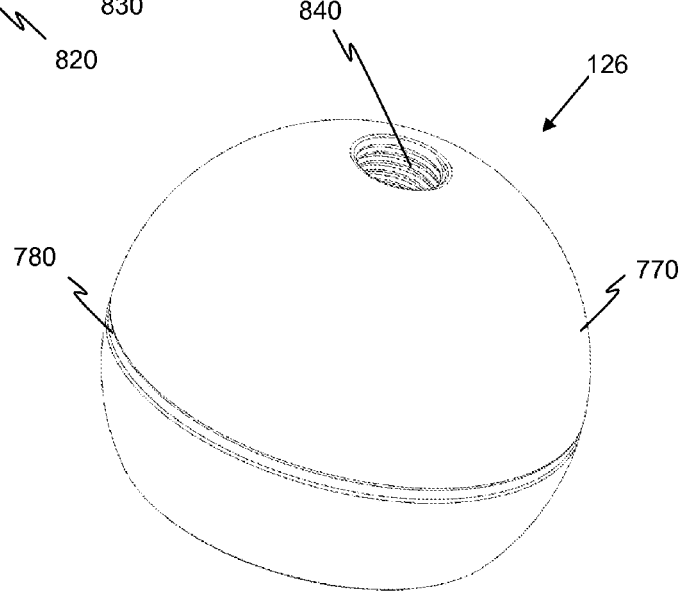

FIG. 8B illustrates a top perspective view of the exemplary shell member 126. As discussed above with reference to FIG. 7, the shell member 126 has a partially spherical outer surface 770 and a groove 780. The shell member 126 further has a threaded aperture 840.

Figures 8C, 8D:
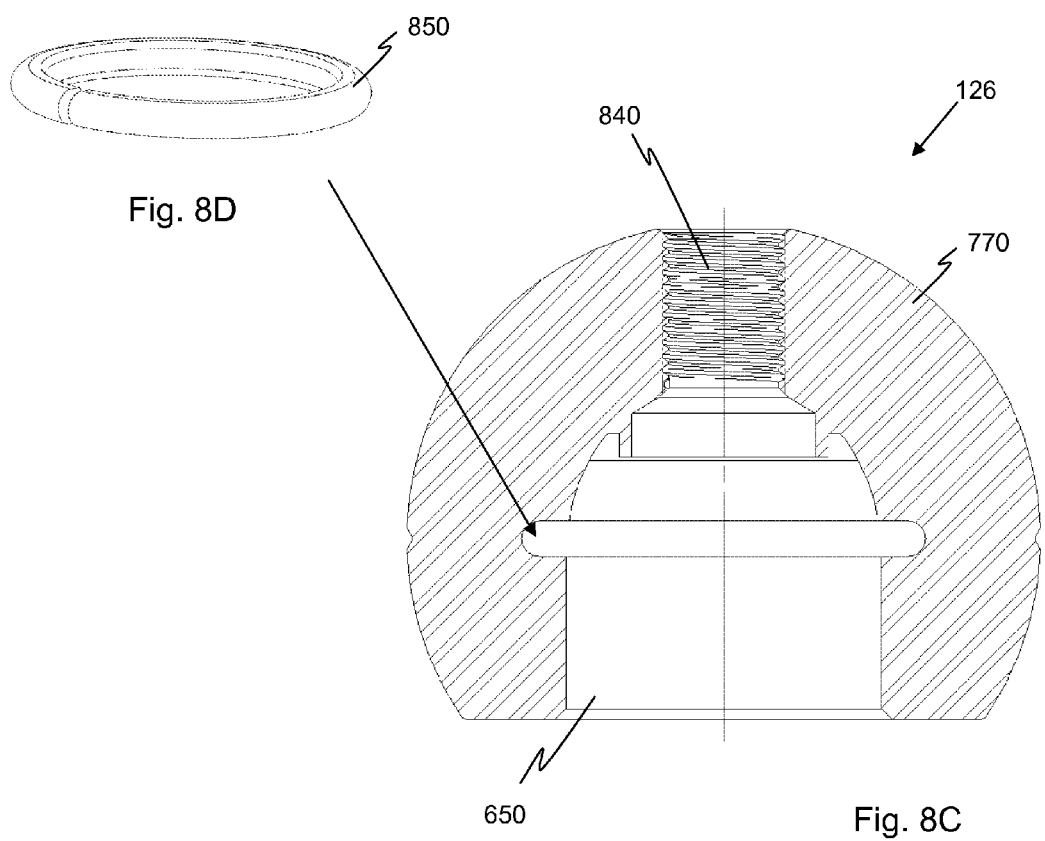
FIG. 8C is a cross-section of an exemplary shell member of the femoral trial system.
FIG. 8D is a perspective view of an annular ring configured to be disposed between a head member and a shell member.

FIG. 8C illustrates a cross-section of the exemplary shell member 126. In addition to the outer surface 770, inner surface 810 and threaded aperture 840, and the shell member 126 is configured to receive an annular ring 850 (shown in perspective in FIG. 8D).

FIGS. 9-16 illustrate cross-sections of exemplary shell members in combination with exemplary head members where the shell member mates with the head member. FIGS. 17A and 17B illustrate perspective views of a specific shell member that does not mate with a specific head member. FIGS. 18-23 illustrate cross-sections of exemplary shell members in combination with exemplary head members where the shell member does not mate with the head member. It should be understood that the illustrated embodiments are merely exemplary. The components may be configured to allow for any combination of a head member and a shell member. In one alternative embodiment (not shown), each head member is configured to mate with each shell member.

Figure 9:
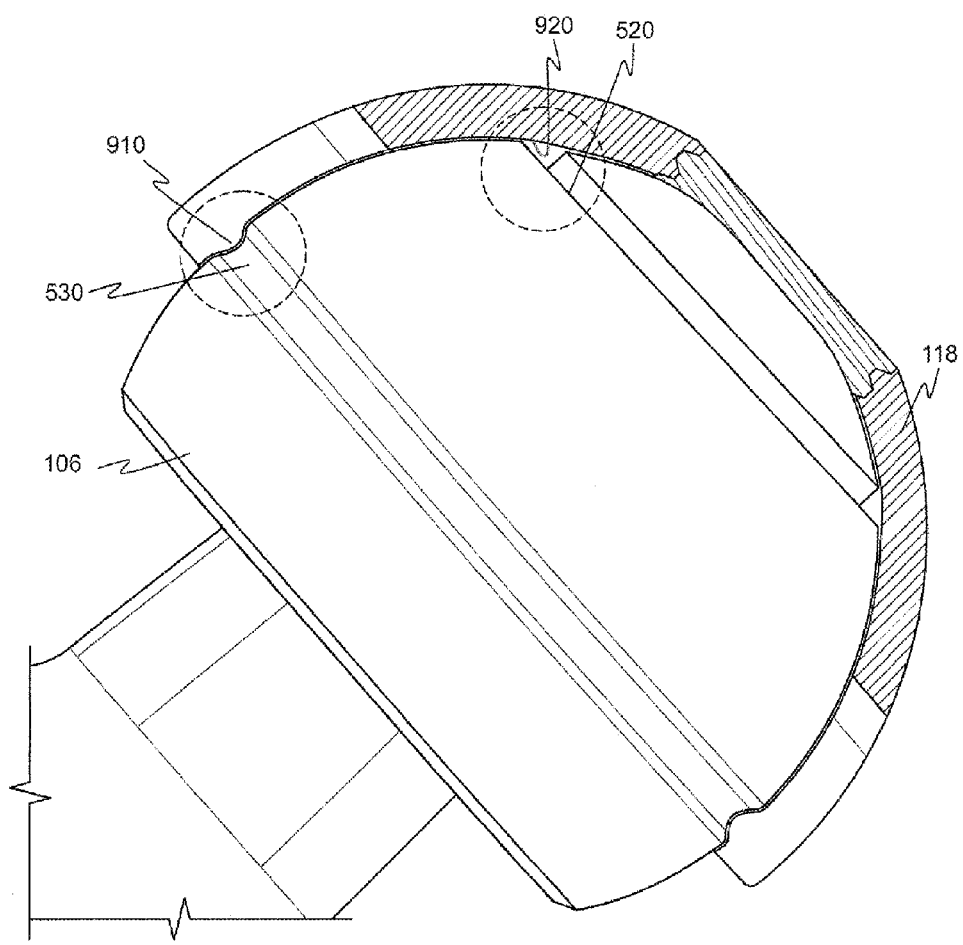
FIGS. 9-16 are cross-sections of specific shell members engaging specific head members.

FIG. 9 illustrates a head member 106 having a −3 mm offset, mated with a shell member 118 having a 32 mm diameter. The shell member 118 includes a rib 910 on its inner surface that is configured to engage the groove 530 of the head member 106. The upper portion of the inner surface of the shell member 118 has a smooth portion 920 that covers the flat portion 520 of the head member 106. Although the smooth portion 920 does not mate with the flat portion 520 of the head member 106, the two portions do not interfere with each other. Accordingly, the shell member 118 is able to fully mate with the head member 106.

Figure 10:
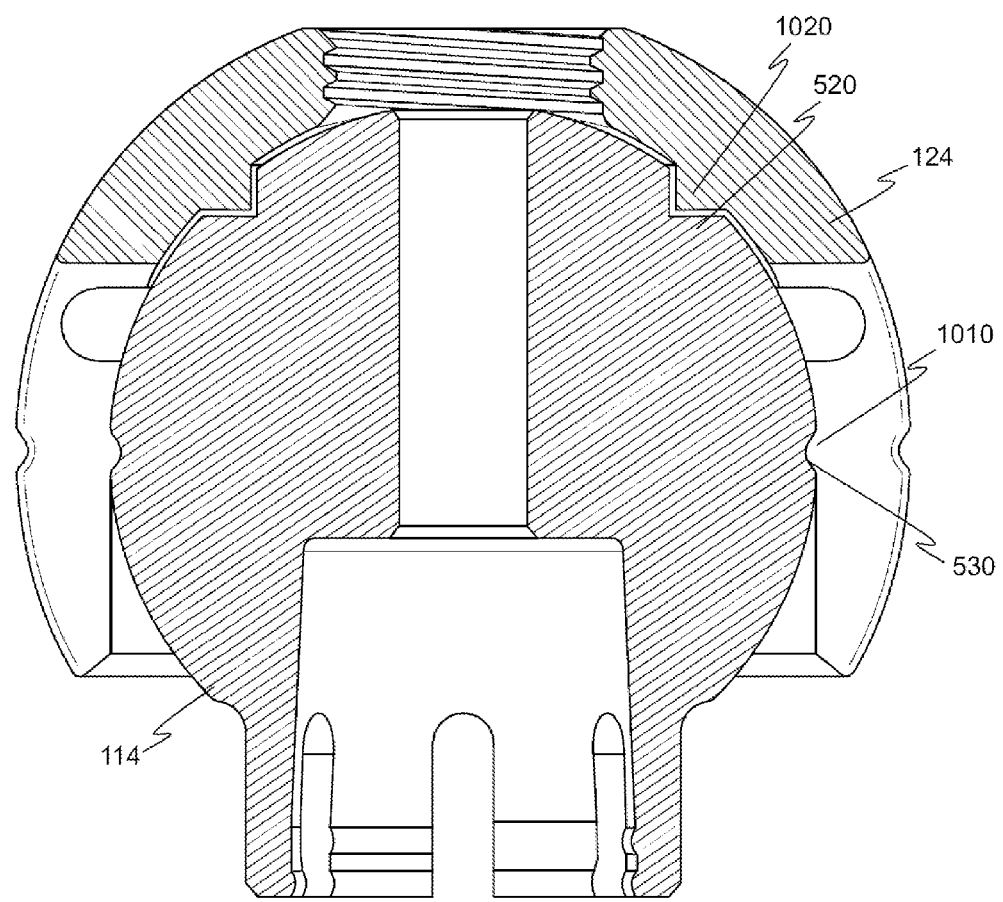

FIG. 10 illustrates a cross-section of a head member 114 having a +11 mm offset, mated with a shell member 124 having a 36 mm diameter. The shell member 124 includes a rib 1010 on its inner surface that is configured to engage the groove 530 of the head member 114. The upper portion of the inner surface of the shell member 124 has a second rib 1020 that corresponds with the flat portion 520 of the head member 114. Accordingly, the shell member 124 is able to fully mate with the head member 114.

Figure 11:
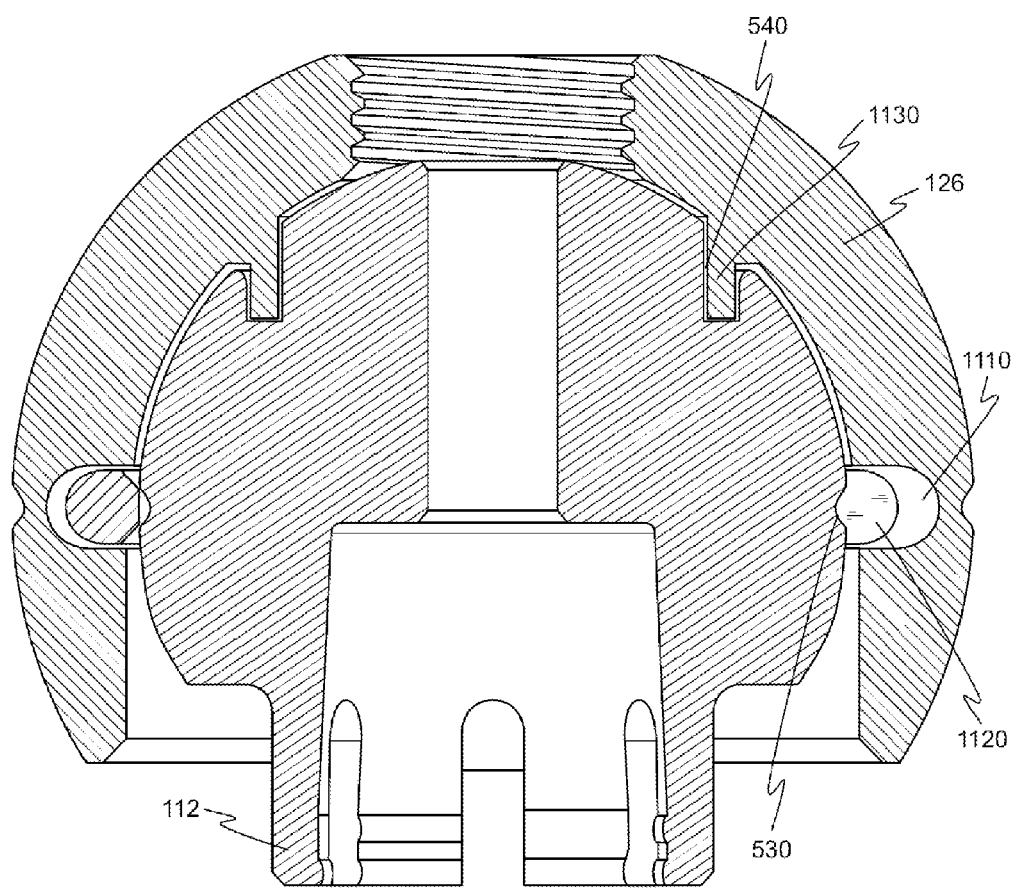

FIG. 11 illustrates a cross-section of a head member 112 having a +8 mm offset, mated with a shell member 126 having a 38 mm diameter. The shell member 126 includes a groove 1110 on its inner surface that is configured to receive an annular ring 1120. The annular ring 1120, in turn, engages the groove 530 of the head member 112. The upper portion of the inner surface of the shell member 126 has a projection 1130 that mates with the recess 540 of the head member 112. Accordingly, the shell member 126 is able to fully mate with the head member 112.

Figure 12:
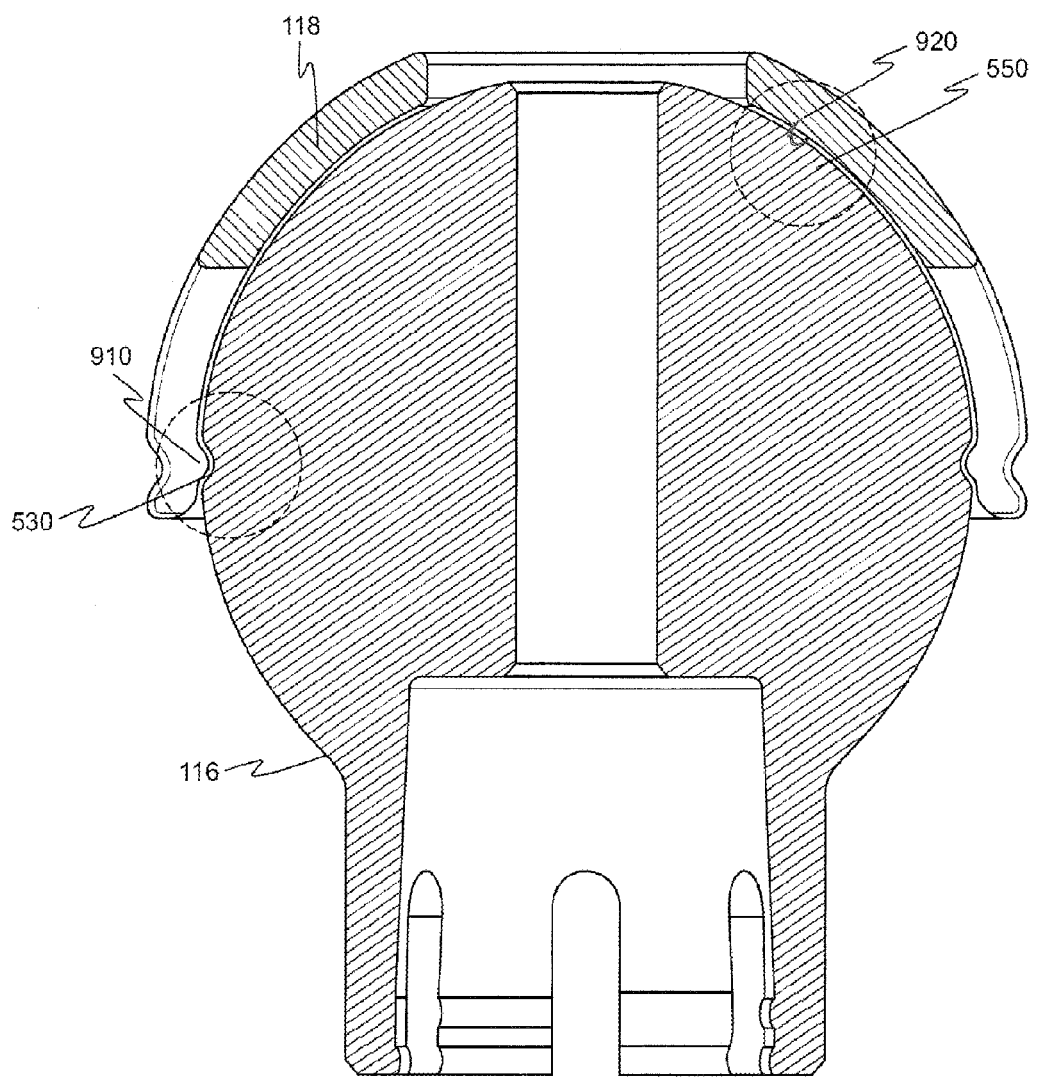

FIG. 12 illustrates a cross-section of a head member 116 having a +15 mm offset, mated with a shell member 118 having a 30 mm diameter. As explained above with reference to FIG. 9, the shell member 118 includes a rib 910 on its inner surface that is configured to engage the groove 530 of the head member 116. The upper portion of the inner surface of the shell member 118 has a smooth portion 920 that covers the smooth outer surface 550 of the head member 116. Accordingly, the shell member 118 is able to fully mate with the head member 116.

Figure 13:
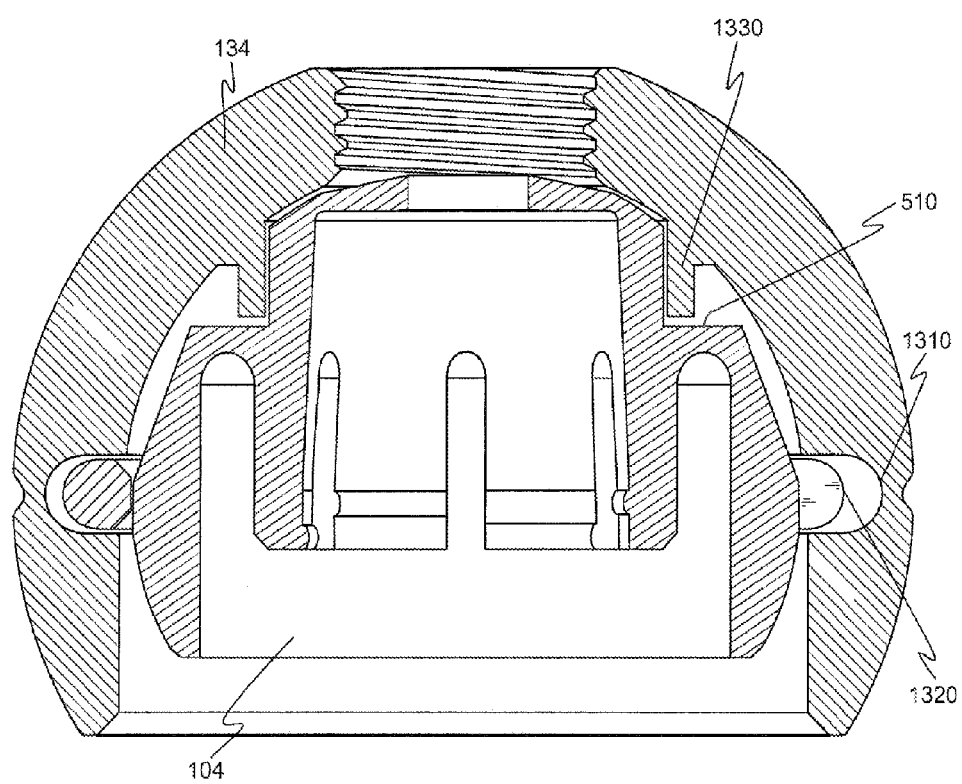

FIG. 13 illustrates a cross-section of a head member 104 having a −4 mm offset, mated with a shell member 134 having a 46 mm diameter. The shell member 134 includes a groove 1310 on its inner surface that is configured to receive an annular ring 1320. The annular ring 1320, in turn, engages the head member 104. The upper portion of the inner surface of the shell member 134 has a projection 1330 that does not interfere with the flat surface 510 of the head member 104. Accordingly, the shell member 134 is able to fully mate with the head member 104.

Figure 14:
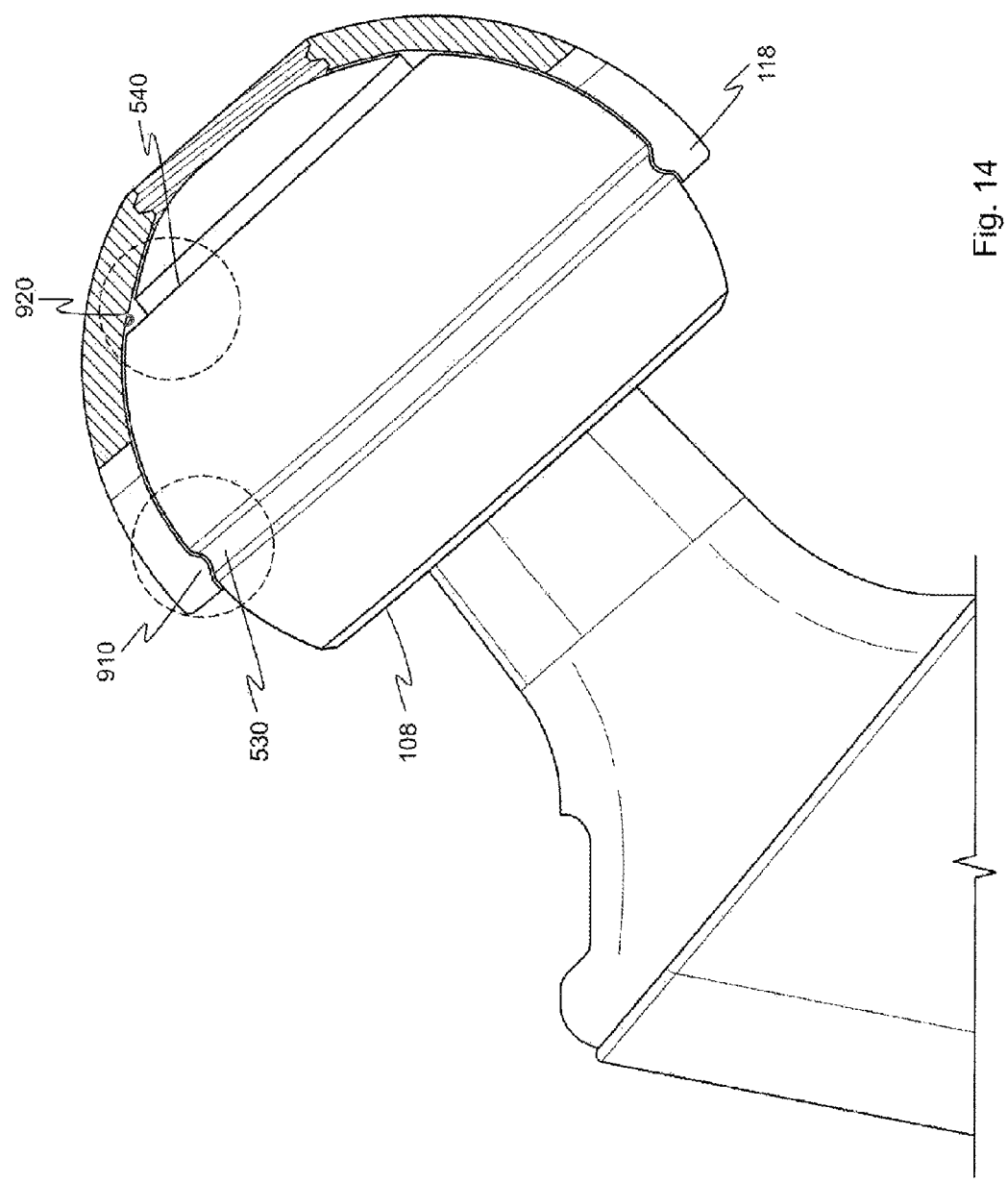

FIG. 14 illustrates a cross-section of a head member 108 having a +0 mm offset, mated with a shell member 118 having a 32 mm diameter. As explained above with reference to FIG. 9, the shell member 118 includes a rib 910 on its inner surface that is configured to engage the groove 530 of the head member 108. The upper portion of the inner surface of the shell member 118 has a smooth portion 920 that covers the recess 540 of the head member 108. Accordingly, the shell member 118 is able to fully mate with the head member 108.

Figure 15:
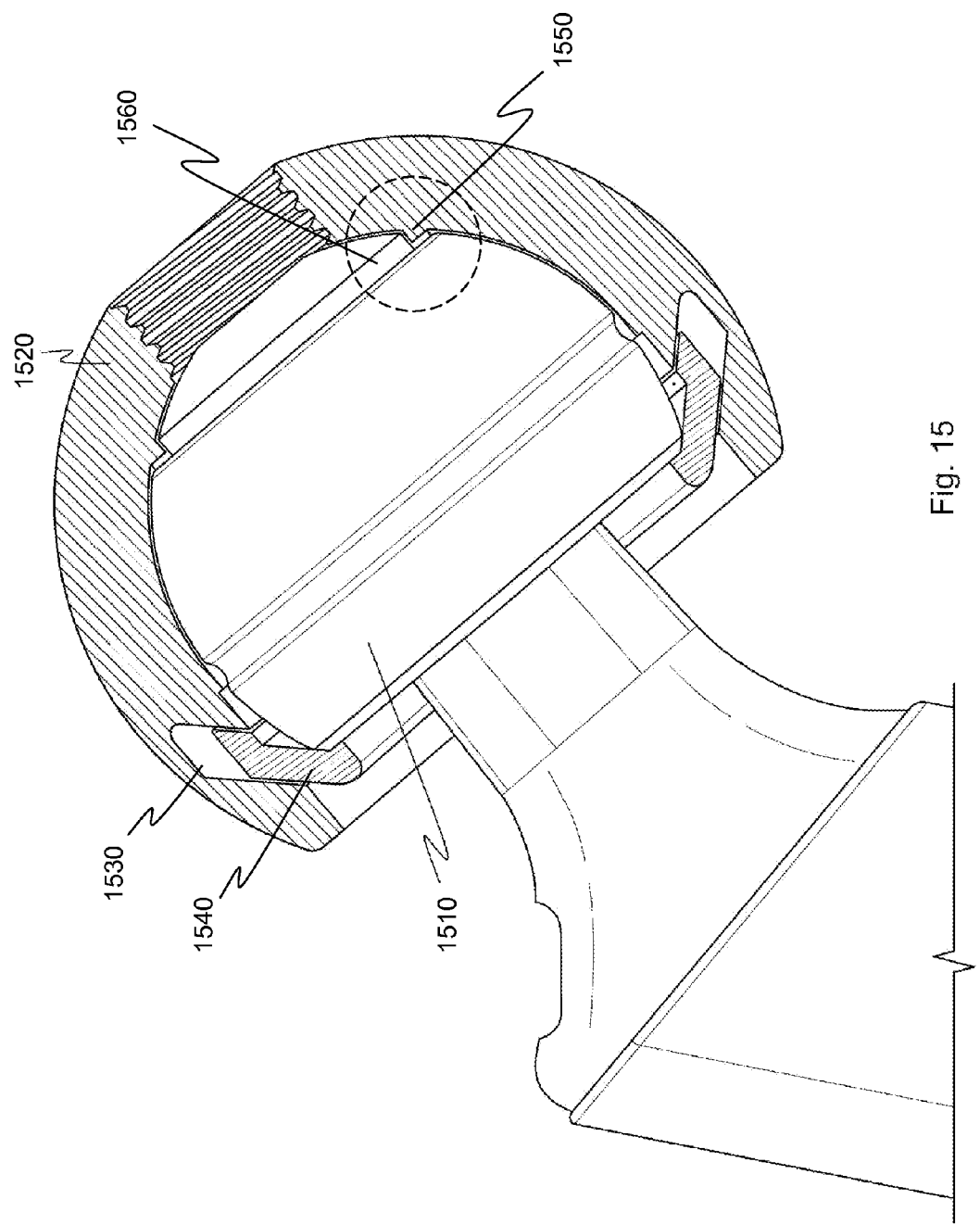

FIG. 15 illustrates a cross-section of an alternative embodiment of a head member 1510 having a +0 mm offset, mated with an alternative embodiment of a shell member 1520 having a 46 mm diameter. The shell member 1520 includes a groove 1530 on its inner surface that is configured to receive an annular ring 1540. The annular ring 1540, in turn, engages an underside of the head member 1510. In the illustrated embodiment, the groove 1530 is an angled groove and the annular ring 1540 has a corresponding angle. In an alternative embodiment, the groove and annular ring have a straight profile.

With continued reference to FIG. 15, the upper portion of the inner surface of the shell member 1520 has a projection 1550 that engages a recess 1560 of the head member 1510. Accordingly, the shell member 1520 is able to fully mate with the head member 1510.

Figure 16:
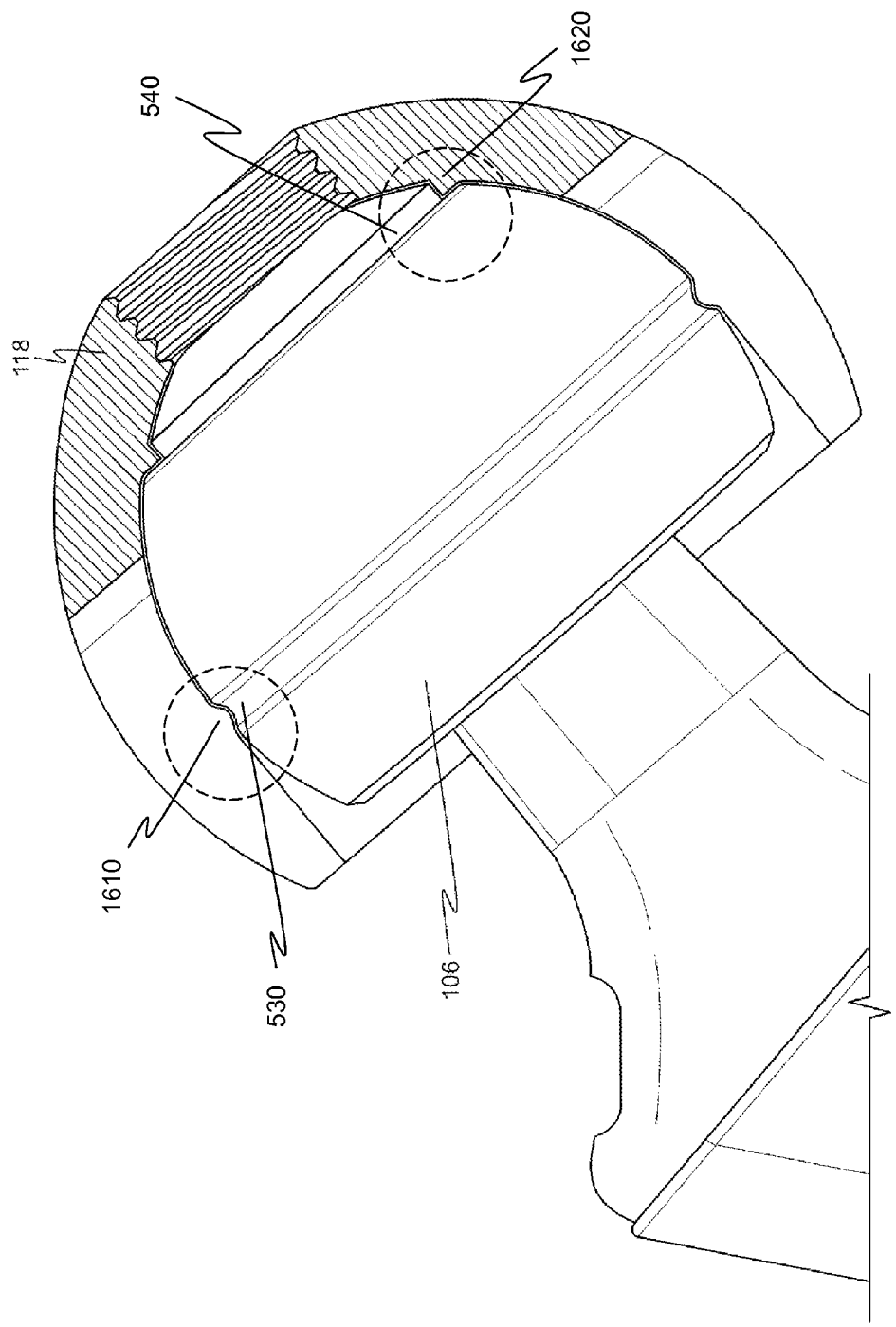
Figure 17A:
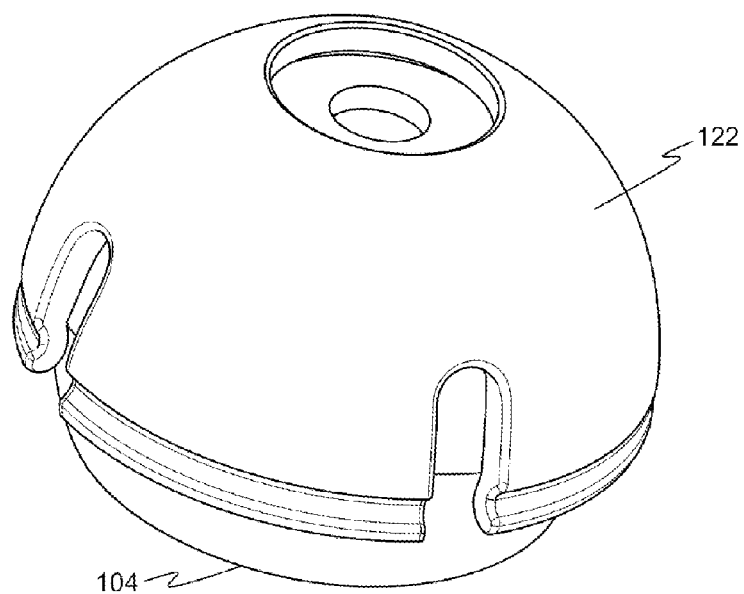
FIGS. 17A and 17B are perspective views of one embodiment of a shell member engaging one embodiment of a head member.
Figure 17B:
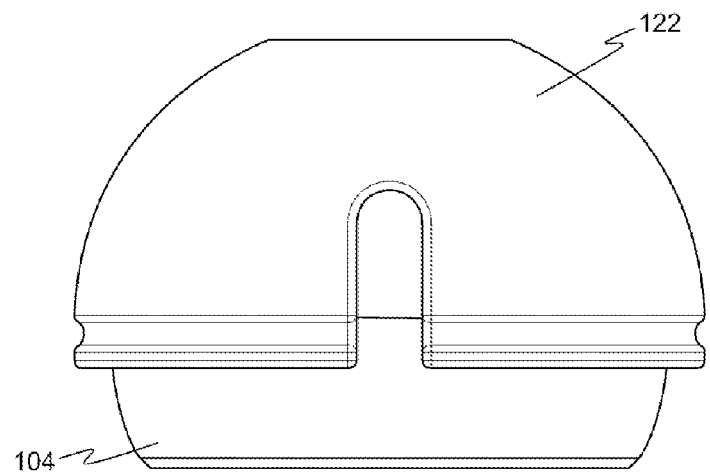

FIG. 16 illustrates a cross-section of a head member 106 having a +0 mm offset, mated with a shell member 118 having a 36 mm diameter. The shell member 118 includes a rib 1610 on its inner surface configured to engage a groove 530 of the head member 106. The upper portion of the inner surface of the shell member 118 has a projection 1620 that engages the recess 540 of the head member 106. Accordingly, the shell member 118 is able to fully mate with the head member 106.

FIGS. 17A and 17B illustrate a perspective view and a side view, respectively, of a 32 mm shell member 122 in combination with a head member 104 having a −4 mm offset. The shell member 122 is unable to mate with the head member 104, for the reasons set forth below.

Figure 18:
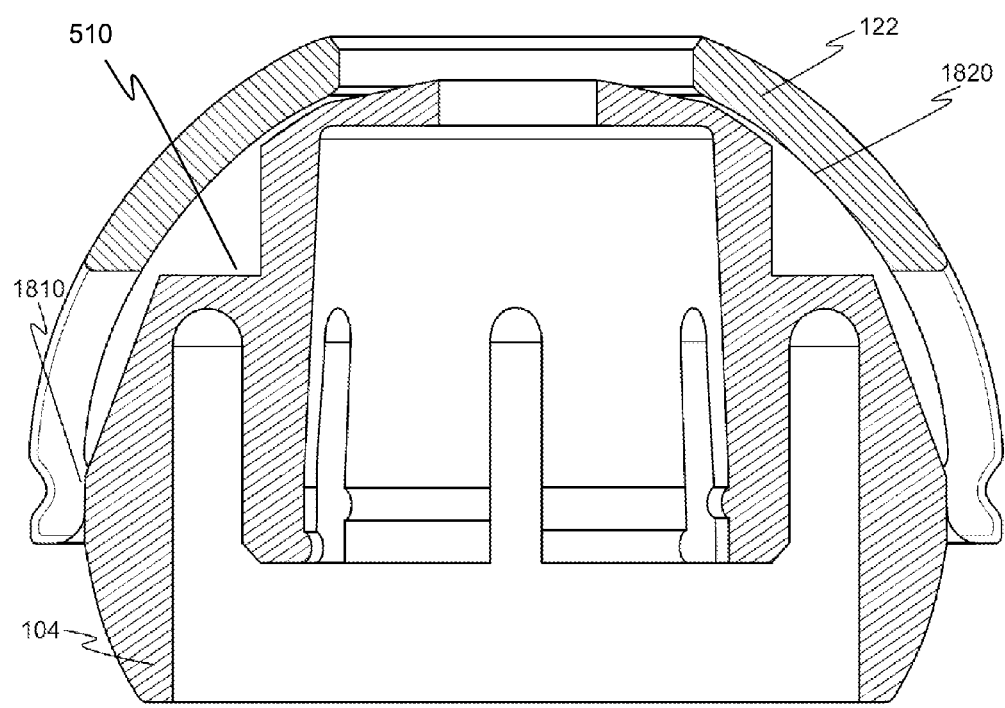
FIGS. 18-23 are cross-sections of combinations of specific shell members that cannot engage specific head members.

FIG. 18 illustrates a cross-section of the 32 mm shell member 122 in combination with the head member 104. The shell member 122 includes a rib 1810 that does not engage in a corresponding groove in the head member 104. The shell member 122 further includes a smooth surface 1820 that does not conform to the flat surface 510 of the head member 104. Therefore, the shell member 122 does not mate with the head member 104.

Figure 19:
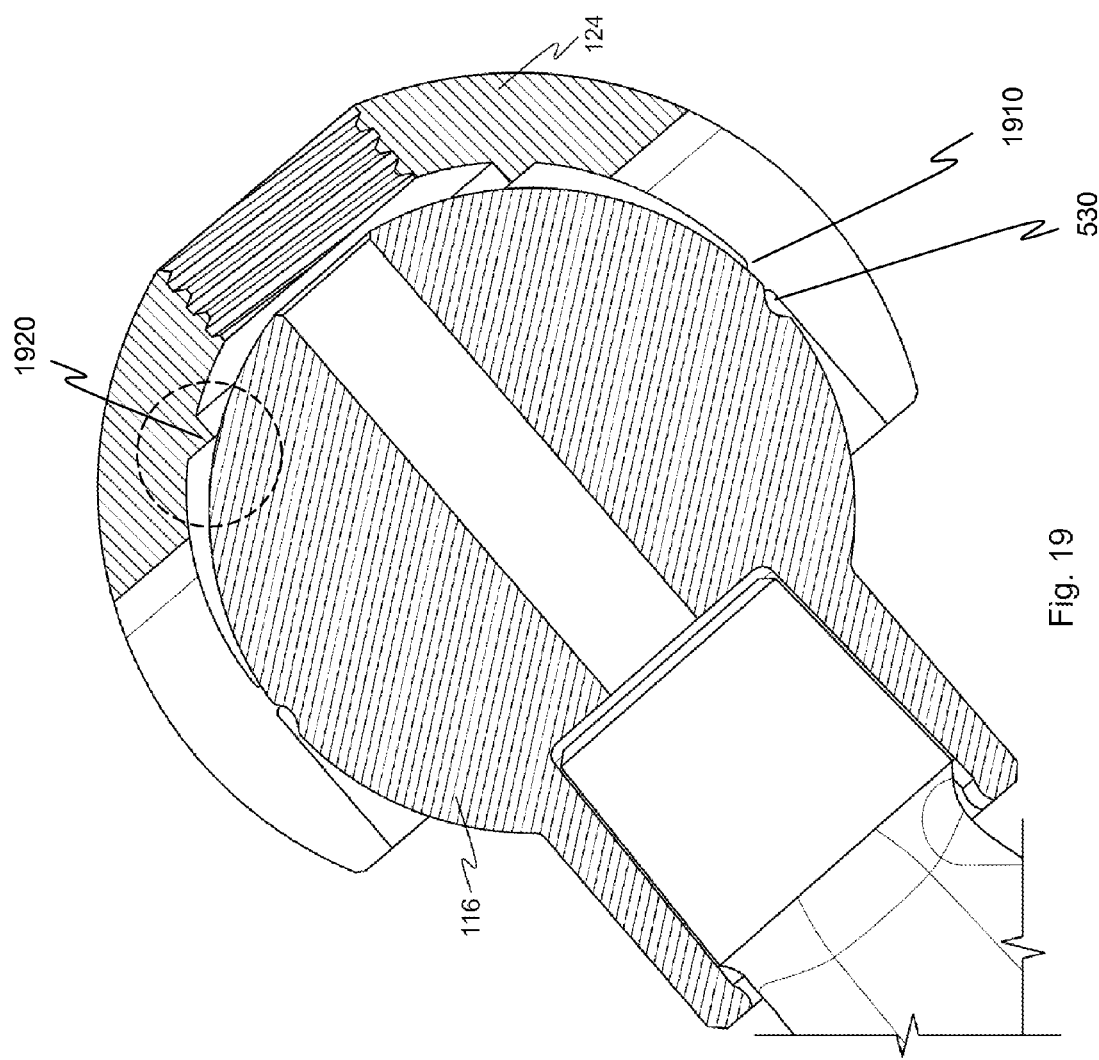
Figure 20:
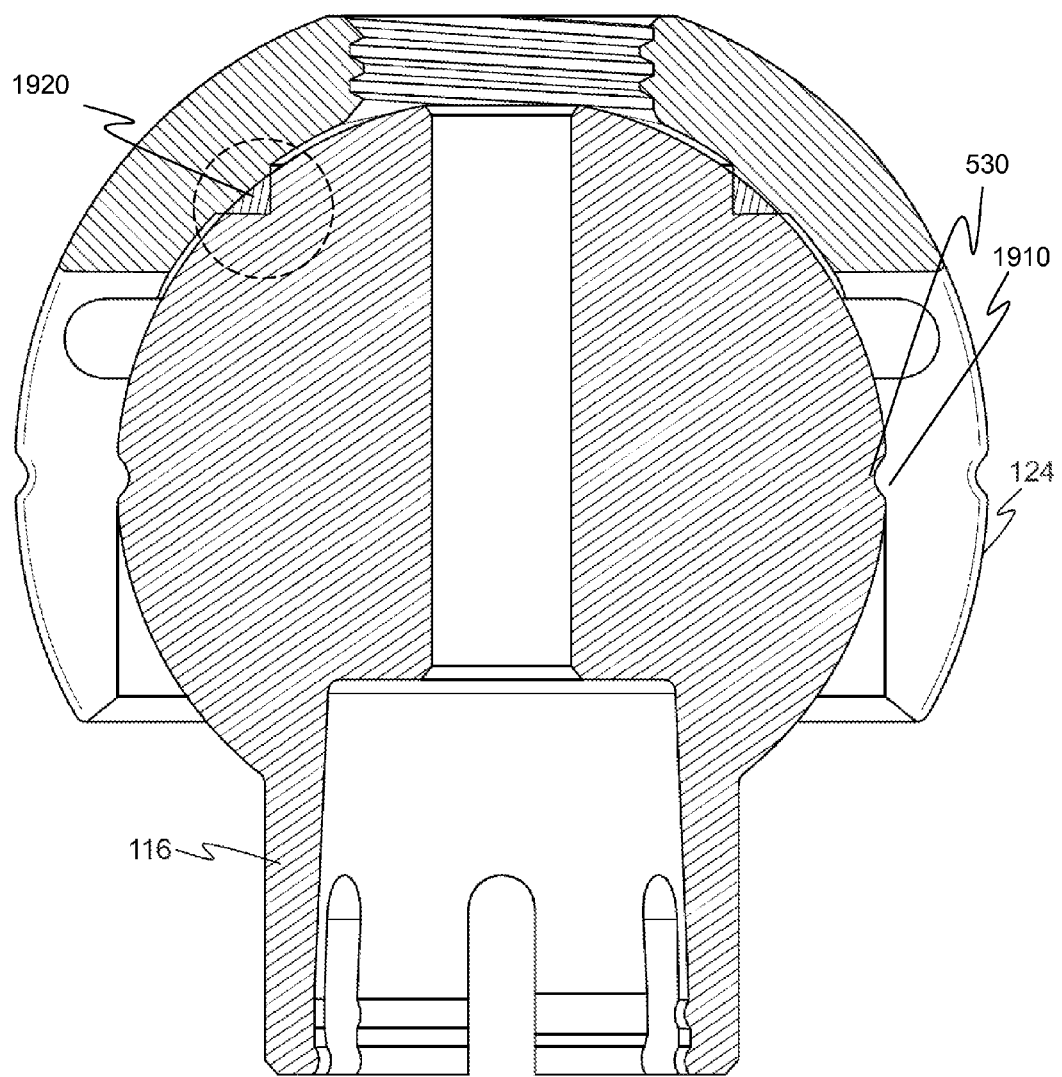

FIGS. 19 and 20 illustrates cross-sections of a head member 116 having a +15 mm offset, in combination with a shell member 124 having a 36 mm diameter. The shell member 124 includes a rib 1910 on its inner surface configured to engage a groove 530 of the head member 116. However, the upper portion of the inner surface of the shell member 124 has a projection 1920 that interferes with the head member 116. Accordingly, the shell member 124 does not mate with the head member 116.

Figure 21:
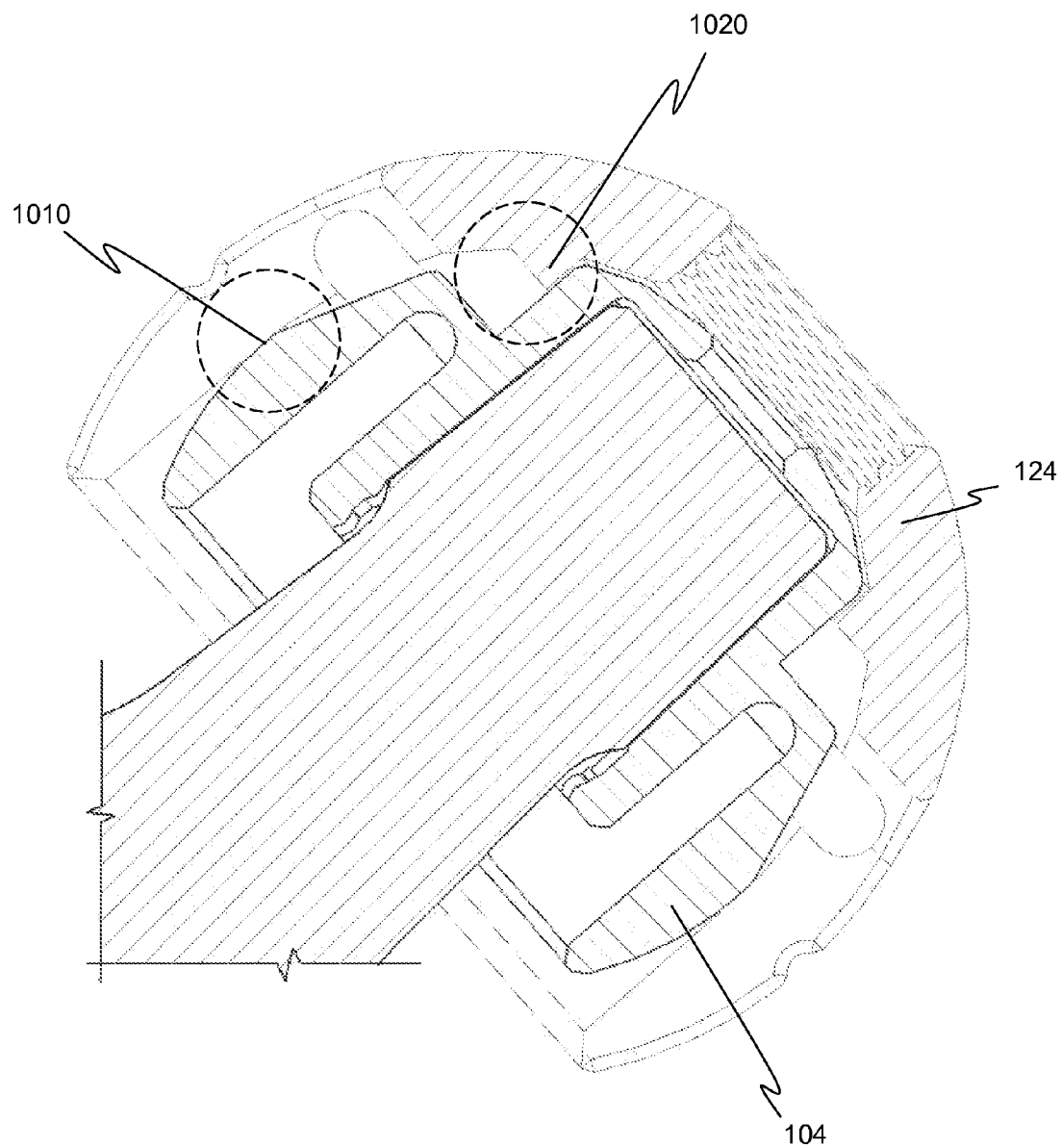

FIG. 21 illustrates a cross-section of a head member 104 having a −4 mm offset, in combination with a shell member 124 having a 36 mm diameter. The shell member 124 includes a rib 1010, but the head member 104 does not have a corresponding groove. Additionally, the head member 104 has a non-spherical geometry that does not conform to the second rib 1020 of the shell member 124. Accordingly, the shell member 124 does not mate with the head member 104.

Figure 22:
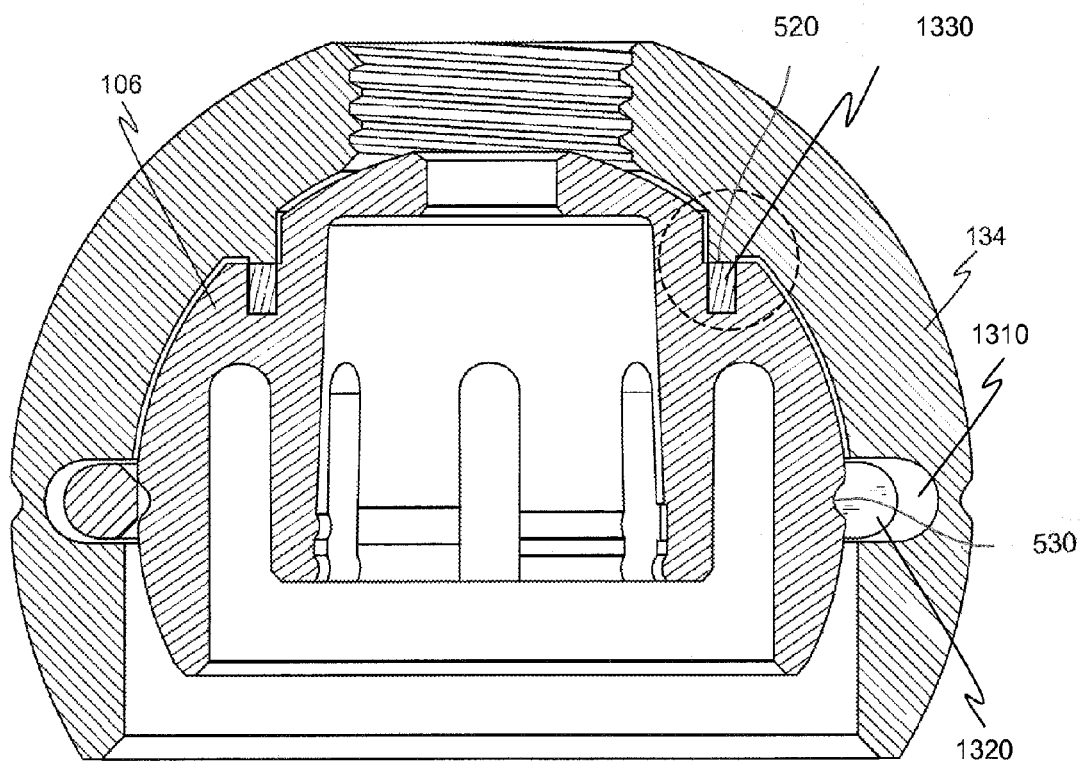

FIG. 22 illustrates a head member 106 having a −3 mm offset, in combination with a shell member 134 having a 46 mm diameter. The shell member 134 includes a groove 1310 on its inner surface that is configured to receive an annular ring 1320. The annular ring 1320, in turn, engages the groove 530 in the head member 106. The upper portion of the inner surface of the shell member 134 has a projection 1330 that interferes with the flat surface 520 of the head member 106. Accordingly, the shell member 134 does not mate with the head member 106.

Figure 23:
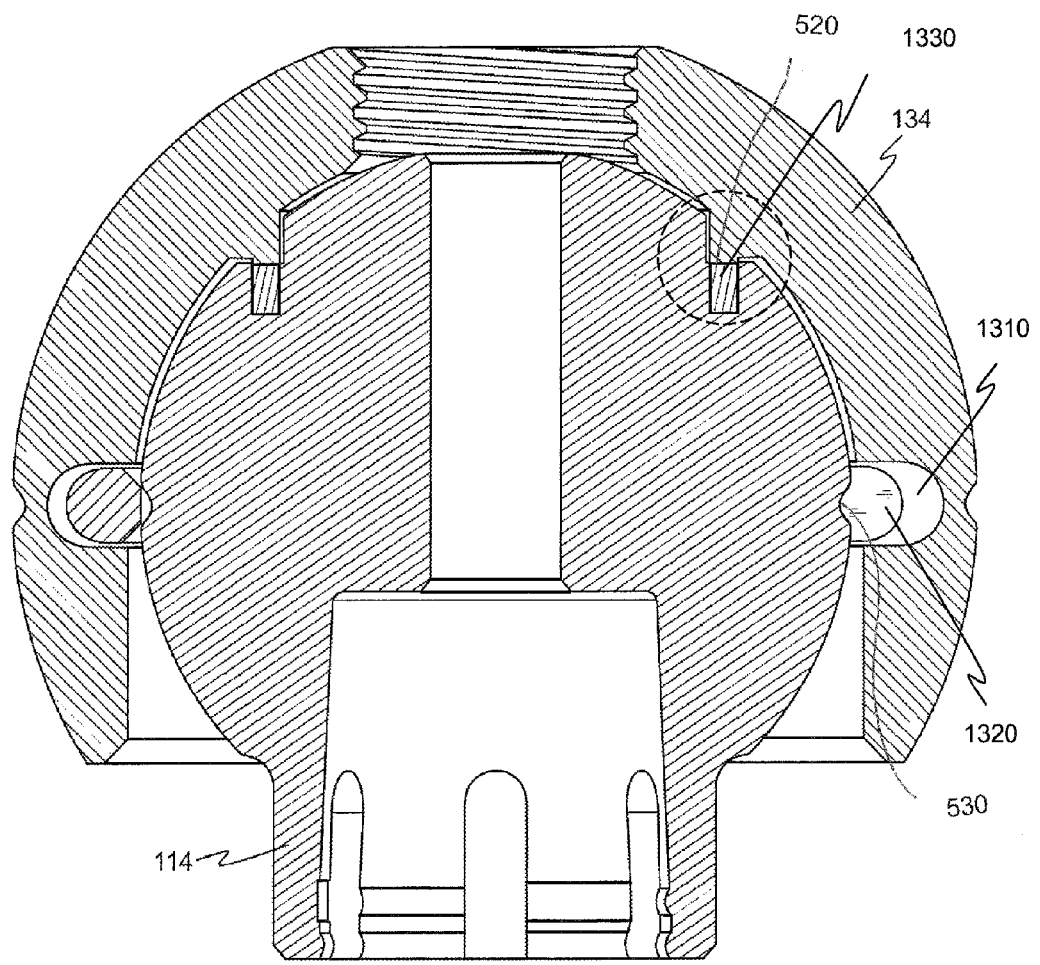

FIG. 23 illustrates a head member 114 having a +11 mm offset, in combination with a shell member 134 having a 46 mm diameter. The shell member 134 includes a groove 1310 on its inner surface that is configured to receive an annular ring 1320. The annular ring 1320, in turn, engages the groove 530 in the head member 114. The upper portion of the inner surface of the shell member 134 has a projection 1330 that interferes with the flat surface 520 of the head member 114. Accordingly, the shell member 134 does not mate with the head member 114.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. A femoral trial system for use with a plurality of stems, the femoral trial system comprising:
   a plurality of head members, each head member having:
      an outer surface;
      a cavity configured to mate with an exterior surface of a stem component, the cavity having at least one sidewall;
      a first set of barbs disposed on the sidewall of the cavity at a first depth; and
      a second set of barbs disposed on the sidewall of the cavity at a second depth spaced apart from the first depth;
      wherein each head member includes a plurality of flexible fingers each extending along a depth of the cavity and each defining a portion of the sidewall and at least one of the barbs; and
   a plurality of shell members, each shell member having an inner surface configured to mate with the outer surface of at least one of the plurality of head members.

2. The femoral trial system of claim 1, wherein the first set of barbs is configured to mate with a corresponding first groove in an exterior surface of a first stem component.

3. The femoral trial system of claim 2, wherein the second set of barbs is configured to mate with a corresponding second groove in an exterior surface of a second stem component.

4. The femoral trial system of claim 1, wherein the plurality of head members includes a first head member having an outer surface with a first outer surface configuration, and a second head member having an outer surface with a second outer surface configuration different from the first outer surface configuration, and wherein the first and second head members each define substantially identical maximum outer surface diameters.

5. The femoral trial system of claim 4, wherein the first outer surface configuration includes a flat portion and the second outer surface configuration includes a recess.

6. The femoral trial system of claim 4, wherein the plurality of shell members includes a first shell member having an inner surface with a first inner surface configuration for mating with the outer surface configuration of the first head member, and a second shell member having an inner surface with a second inner surface configuration for mating with the second outer surface configuration of the second head member, and wherein the first and second shell members each have an inner surface diameter corresponding to the maximum outer surface diameter of the first and second head members.

7. The femoral trial system of claim 6, wherein the first inner surface configuration of the first shell member is configured to not mate with the second outer surface configuration of the second head member.

8. The femoral trial system of claim 1, wherein the outer surface of at least one of the plurality of head members is at least partially spherical.

9. The femoral trial system of claim 1, wherein the inner surface of each of the plurality of shell members is at least partially spherical.

10. The femoral trial system of claim 1, wherein the first and second sets of barbs comprise individual barb elements spaced apart from one another along a depth of the cavity.

11. The femoral trial system of claim 1, wherein the first and second sets of barbs comprise individual ribs each extending inwardly from the sidewall and spaced apart from one another along a depth of the cavity.

12. The femoral trial system of claim 1, wherein the first and second sets of barbs are spaced apart from one another by a recess.

13. The femoral trial system of claim 1, wherein the first and second sets of barbs each have a round profiled and are spaced apart from one another by a rounded recess.

14. The femoral trial system of claim 1, wherein a first of the flexible fingers includes a barb from the first set of barbs and also includes a barb from the second set of barbs, and wherein a second of the flexible fingers includes a barb from the first set of barbs but does not include a barb from the second set of barbs.

15. The femoral trial system of claim 1, wherein a first of the shell members and a first of the head members include structural features that interact with one another to allow the inner surface of the first shell member to fully engage and mate with the outer surface of the first head member; and
  wherein the first shell member and a second of the head members include structural features that interact with one another to prevent the inner surface of the first shell member to fully engage the outer surface of the second head member; and
  wherein the structural features of the first shell member and the first head member that interact with one another to allow the inner surface of the first shell member to fully engage and mate with the outer surface of the first head member comprise at least one pair of corresponding projections and grooves.

16. The femoral trial system of claim 1, wherein a first of the shell members and a first of the head members include structural features that interact with one another to allow the inner surface of the first shell member to fully engage and mate with the outer surface of the first head member; and
  wherein the first shell member and a second of the head members include structural features that interact with one another to prevent the inner surface of the first shell member to fully engage the outer surface of the second head member; and
  wherein the structural features of the first shell member and the first head member that interact with one another to allow the inner surface of the first shell member to fully engage and mate with the outer surface of the first head member comprise at least one pair of corresponding flatted surfaces and recesses.

17. The femoral trial system of claim 1, wherein the plurality of flexible fingers flex radially outward to receive a portion of the stem component within the cavity.

18. A femoral trial system for use with a plurality of stems, the femoral trial system comprising:
  a plurality of head members, each head member having:
    an outer surface;
    a cavity configured to mate with an exterior surface of a stem component, the cavity having at least one sidewall;
    a first set of barbs disposed on the sidewall of the cavity at a first depth; and
    a second set of barbs disposed on the sidewall of the cavity at a second depth spaced apart from the first depth; and
  a plurality of shell members, each shell member having an inner surface configured to mate with the outer surface of at least one of the plurality of head members;
  wherein the plurality of head members includes a first head member having an outer surface with a first outer surface configuration, and a second head member having an outer surface with a second outer surface configuration different from the first outer surface configuration, and wherein the first and second head members each define substantially identical maximum outer surface diameters;
  wherein the plurality of shell members includes a first shell member having an inner surface with a first inner surface configuration for mating with the outer surface configuration of the first head member, and a second shell member having an inner surface with a second inner surface configuration for mating with the second outer surface configuration of the second head member, and wherein the first and second shell members each have an inner surface diameter corresponding to the maximum outer surface diameter of the first and second head members; and
  wherein the second inner surface configuration of the second shell member is configured to not mate with the first outer surface configuration of the first head member.

19. A femoral trial system for use with a plurality of stems, the femoral trial system comprising:
  a plurality of head members, each head member having:
    an outer surface;

a cavity configured to mate with an exterior surface of a stem component, the cavity having at least one sidewall;

a first set of barbs disposed on the sidewall of the cavity at a first depth; and a second set of barbs disposed on the sidewall of the cavity at a second depth spaced apart from the first depth; and a plurality of shell members, each shell member having an inner surface configured to mate with the outer surface of at least one of the plurality of head members;

wherein the plurality of head members includes a first head member having an outer surface with a first outer surface configuration, and a second head member having an outer surface with a second outer surface configuration different from the first outer surface configuration, and wherein the first and second head members each define substantially identical maximum outer surface diameters;

wherein the plurality of shell members includes a first shell member having an inner surface with a first inner surface configuration for mating with the outer surface configuration of the first head member, and a second shell member having an inner surface with a second inner surface configuration for mating with the second outer surface configuration of the second head member, and wherein the first and second shell members each have an inner surface diameter corresponding to the maximum outer surface diameter of the first and second head members; and an annular ring disposed between the second shell member and the second head member.

20. A femoral trial for use in a trial fitting of a medical implant, the femoral trial comprising:

a head member having a cavity disposed therein, wherein the cavity is configured to mate with an exterior surface of a stem component, and wherein the cavity has at least one sidewall;

a first barb disposed on the sidewall of the cavity at a first depth; and a second barb disposed on the sidewall of the cavity at a second depth, the second depth being different than the first depth; and wherein the head member includes a plurality of flexible fingers each extending along a depth of the cavity and each defining a portion of the sidewall and at least one of the first and second barbs.

21. The femoral trial of claim 20, wherein the first barb is configured to mate with a first groove formed in an exterior surface of a first stem component.

22. The femoral trial of claim 21, wherein the second barb is configured to mate with a second groove formed in an exterior surface of a second stem component.

23. The femoral trial of claim 20, further comprising at least one shell member having a cavity configured to mate with an outer surface of the head member.

24. The femoral trial of claim 20, wherein the first and second barbs comprise individual barb elements each extending inwardly from the sidewall and spaced apart from one another along a depth of the cavity.

25. The femoral trial of claim 20, wherein the first and second barbs comprise individual ribs each extending inwardly from the sidewall and spaced apart from one another along a depth of the cavity.

26. The femoral trial of claim 20, wherein the first and second barbs are spaced apart from one another by a recess.

27. The femoral trial of claim 20, wherein the first and second barbs each have a round profiled and are spaced apart from one another by a rounded recess.

28. The femoral trial of claim 20, wherein a first of the flexible fingers includes one of the first barb and also includes one of the second barb, and wherein a second of the flexible fingers includes one of the first barb but does not include any of the second barb.

29. The femoral trial of claim 20, wherein the plurality of flexible fingers flex radially outward to receive a portion of the stem component within the cavity.

* * * * *